(12) United States Patent
Korpas et al.

(10) Patent No.: US 11,147,983 B2
(45) Date of Patent: Oct. 19, 2021

(54) PAIN RELIEF UTILIZING POLYMER BASED MATERIALS OR A COMBINATION OF LED BULBS, POLYMER BASED MATERIALS AND A NEAR FIELD ACCELERATOR

(71) Applicants: E.K. Licensing, LLC, Westland, MI (US); Jack William Shirlin, Garden City, MI (US)

(72) Inventors: Emery Korpas, Westland, MI (US); Jack William Shirlin, Garden City, MI (US)

(73) Assignees: E.K. Licensing, LLC, Plymouth, MI (US); Jack William Shirlin, Garden City, MI (US)

( * ) Notice: Subject to any disclaimer, the term of this patent is extended or adjusted under 35 U.S.C. 154(b) by 0 days.

(21) Appl. No.: 16/872,988

(22) Filed: May 12, 2020

(65) Prior Publication Data

US 2020/0353284 A1   Nov. 12, 2020

Related U.S. Application Data

(60) Division of application No. 15/729,259, filed on Oct. 10, 2017, now Pat. No. 10,702,704, which is a continuation-in-part of application No. 15/599,822, filed on May 19, 2017, now Pat. No. 10,548,977.

(60) Provisional application No. 62/339,570, filed on May 20, 2016, provisional application No. 62/406,146, filed on Oct. 10, 2016.

(51) Int. Cl.
*A61N 5/06*   (2006.01)
*A61N 5/073*   (2006.01)
*A61N 5/067*   (2006.01)

(52) U.S. Cl.
CPC .......... *A61N 5/0622* (2013.01); *A61N 5/0619* (2013.01); *A61N 5/067* (2021.08); *A61N 2005/0642* (2013.01); *A61N 2005/0645* (2013.01); *A61N 2005/0652* (2013.01); *A61N 2005/073* (2013.01)

(58) Field of Classification Search
CPC ..................................................... A61N 5/062
See application file for complete search history.

(56) References Cited

U.S. PATENT DOCUMENTS

| 4,906,849 A | 3/1990 | Duo et al. |
| 5,487,739 A | 1/1996 | Aebischer et al. |
| 6,179,826 B1 | 1/2001 | Aebischer et al. |

(Continued)

FOREIGN PATENT DOCUMENTS

WO   WO-2014022049 A1 *  2/2014  ............... G02C 7/10

OTHER PUBLICATIONS

Eccles (The Journal of Alternative and Complementary Medicinan, vol. 11, No. 2, A Critical Review of Randomized Controlled Trials of Static Magnets for Pain Relief) (Year: 2005).

*Primary Examiner* — Benjamin J Packard
(74) *Attorney, Agent, or Firm* — Howard & Howard Attorneys PLLC

(57) ABSTRACT

A pain relief device and method or system to aid in the resolution of pain in a body including at least one layer of PVDF film and at least one other layer for directional purposes, as well as a polarizing layer. The device can be packaged in various ways. Also described is a device that uses a combination of LED bulbs, polymer based materials and a near field accelerator to provide pain relief.

16 Claims, 21 Drawing Sheets

(56) References Cited

U.S. PATENT DOCUMENTS

| | | |
|---|---|---|
| 6,455,140 B1 | 9/2002 | Whitney et al. |
| 6,475,609 B1 | 11/2002 | Whitney et al. |
| 6,628,989 B1 | 9/2003 | Penner et al. |
| 6,942,634 B2 | 9/2005 | Odland |
| 7,283,874 B2 | 10/2007 | Penner |
| 7,424,325 B2 | 9/2008 | Koller et al. |
| 7,812,025 B2 | 10/2010 | Matsumoto et al. |
| 7,883,535 B2 | 2/2011 | Cantin et al. |
| 7,930,031 B2 | 4/2011 | Penner |
| 7,947,270 B2 | 5/2011 | Franklin |
| 7,951,831 B2 | 5/2011 | Hammock et al. |
| 7,952,349 B2 | 5/2011 | Huang et al. |
| 8,088,163 B1 | 1/2012 | Kleiner |
| 8,277,510 B2 | 10/2012 | Kleiner |
| 8,292,960 B2 | 10/2012 | Kleiner |
| 8,337,485 B2 | 12/2012 | Ludlow et al. |
| 8,343,189 B2 | 1/2013 | Assell et al. |
| 8,343,536 B2 | 1/2013 | Bates et al. |
| 8,557,163 B2 | 10/2013 | Chian et al. |
| 8,574,146 B2 | 11/2013 | Gillespie, Jr. et al. |
| 8,577,460 B2 | 11/2013 | Penner |
| 8,708,701 B2 | 4/2014 | Levens et al. |
| 8,715,355 B2 | 5/2014 | Kleiner |
| 8,721,520 B2 | 5/2014 | Caira et al. |
| 8,758,798 B2 | 6/2014 | Stopek et al. |
| 8,758,799 B2 | 6/2014 | Stopek et al. |
| 8,758,800 B2 | 6/2014 | Stopek et al. |
| 8,808,305 B2 | 8/2014 | Kleiner |
| 8,883,218 B2 | 11/2014 | Radominiska-Pandya et al. |
| 8,896,211 B2 | 11/2014 | Tomer et al. |
| 8,934,972 B2 | 1/2015 | Penner |
| 8,980,302 B2 | 3/2015 | Stopek et al. |
| 9,011,754 B2 | 4/2015 | Leong et al. |
| 9,044,209 B2 | 6/2015 | Dayton et al. |
| 9,044,397 B2 | 6/2015 | Choi et al. |
| 9,050,265 B2 | 6/2015 | Jamison et al. |
| 9,057,068 B1 | 6/2015 | Chapelle et al. |
| 9,271,824 B2 | 3/2016 | Ludlow et al. |
| 9,314,618 B2 | 4/2016 | Imran et al. |
| 2004/0011685 A1 | 1/2004 | Lux, Jr. et al. |

\* cited by examiner

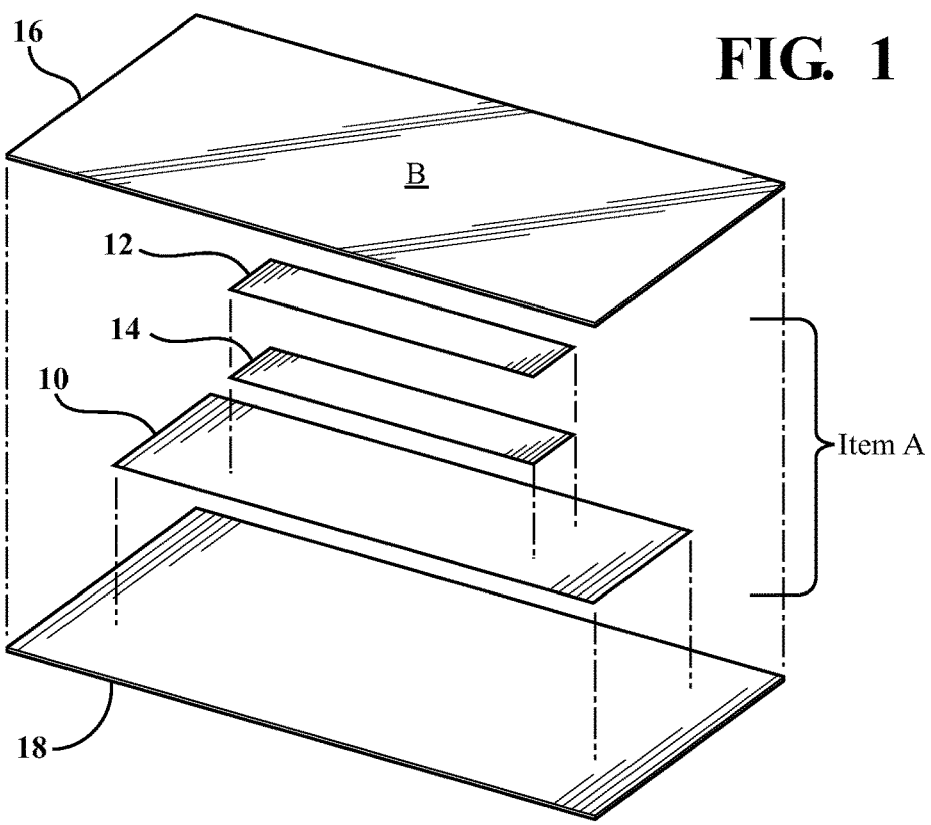
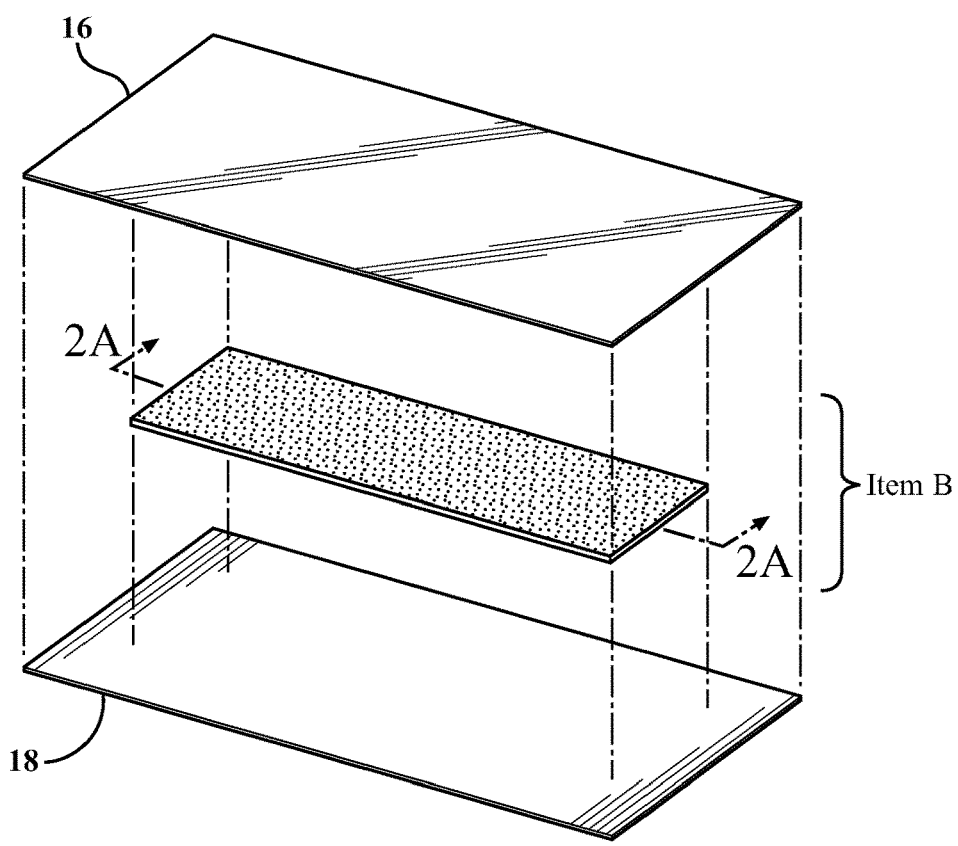

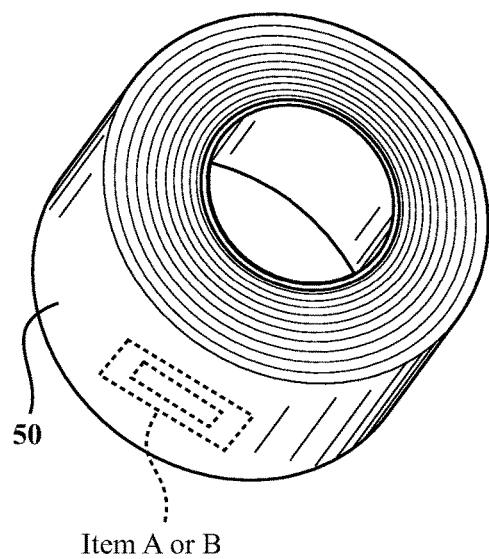
FIG. 3A
Item A or B
FIG. 3B
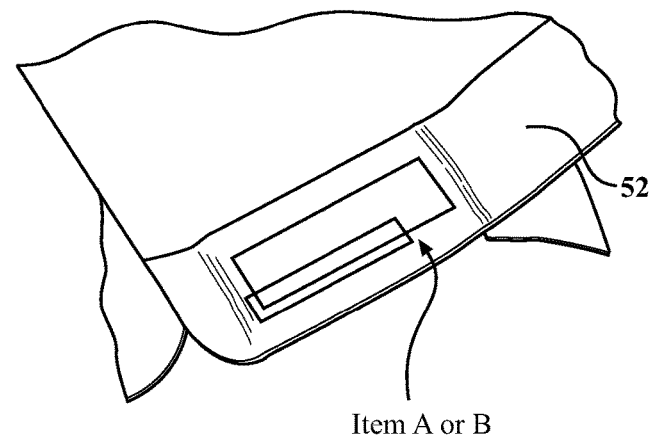
Item A or B
FIG. 3C
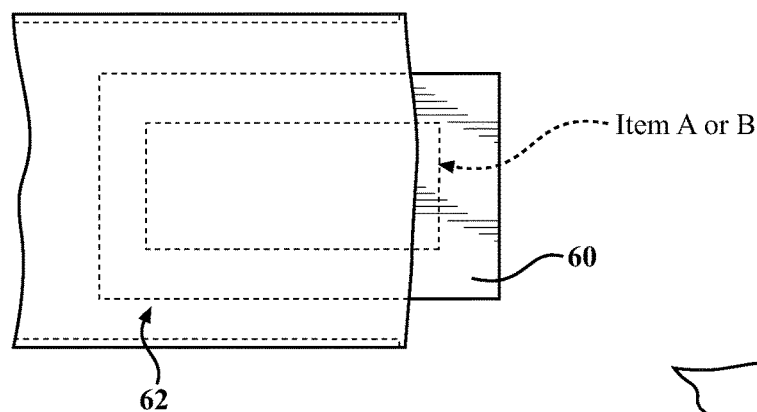
Item A or B
FIG. 3D
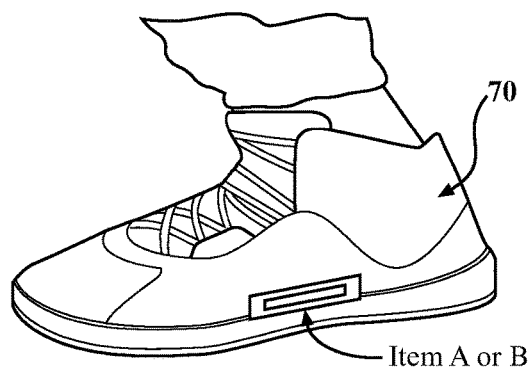
Item A or B

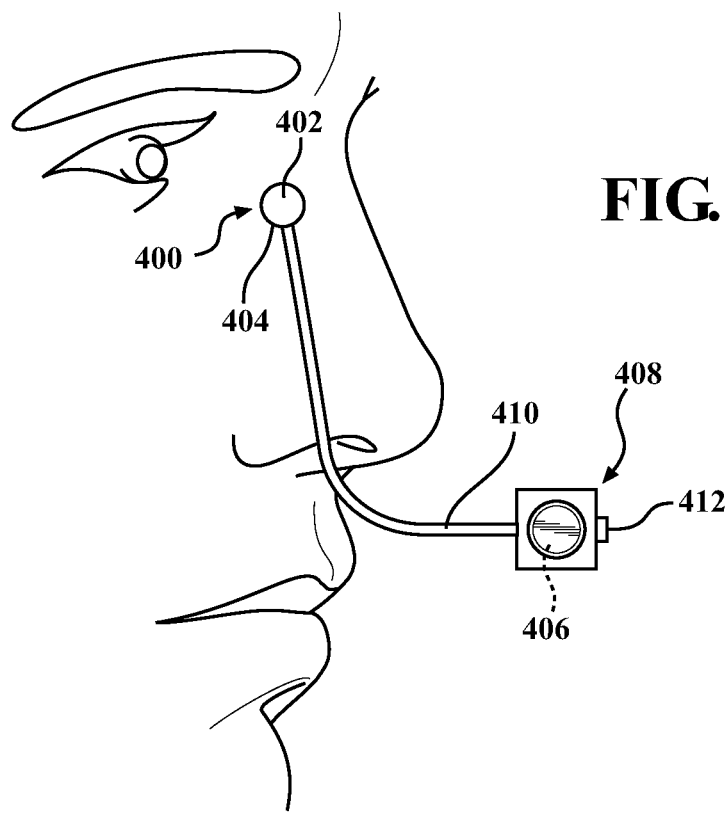
FIG. 6G
FIG. 6H
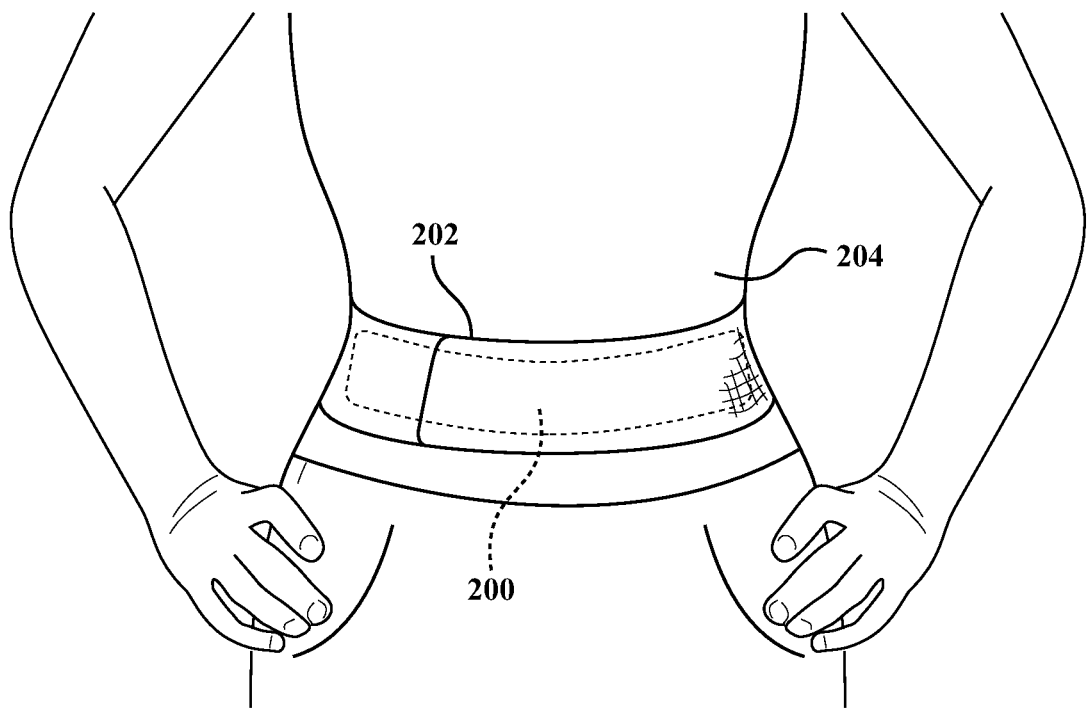

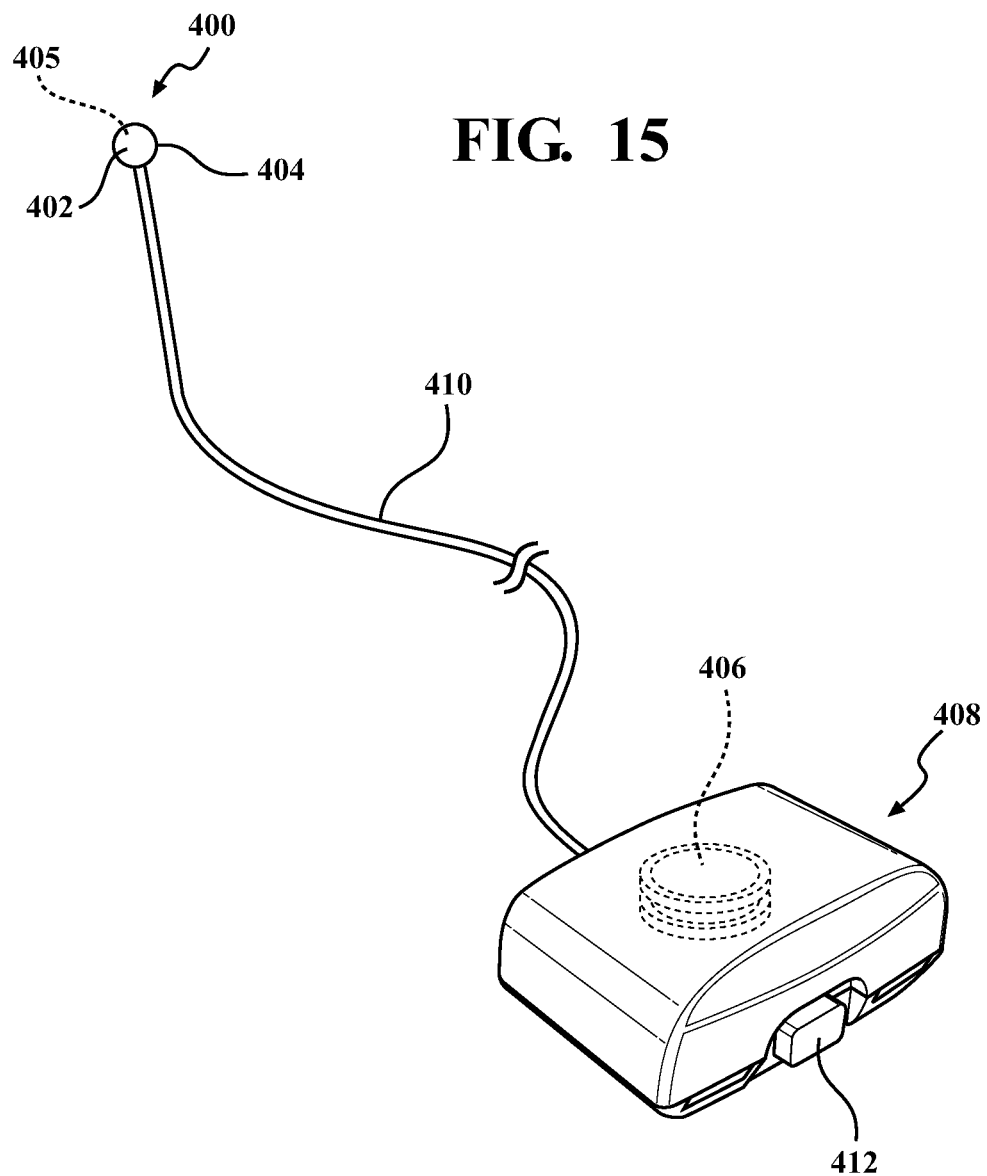

PAIN RELIEF UTILIZING POLYMER BASED MATERIALS OR A COMBINATION OF LED BULBS, POLYMER BASED MATERIALS AND A NEAR FIELD ACCELERATOR

RELATED APPLICATIONS

This application is a divisional application of U.S. Continuation-in-Part patent application Ser. No. 15/729,259, filed on Oct. 10, 2017, which claims priority to and the benefit of continuation-in-part of U.S. patent application Ser. No. 15/599,822, filed on May 19, 2017, which was issued as U.S. Pat. No. 10,548,977 on Feb. 4, 2020, which claims priority to U.S. Provisional Patent Application No. 62/339, 570, filed on May 20, 2016. U.S. patent application Ser. No. 15/599,822, filed on May 19, 2017, also claims priority to and the benefit of U.S. Provisional Patent Application No. 62/406,146, filed on Oct. 10, 2016, which the entire contents of all of the above are hereby incorporated by reference.

TECHNICAL FIELD

The invention relates to products to relieve pain. The invention presented here is not ingested nor is it inserted beyond the skin of the body. It is preferred that the devices be used only external of the outer skin and have been shown to be effective at pain relief in that manner.

A pain relief item is also disclosed that is a light therapy device, but with projection of LED bulbs within close proximity of a scalar wave material. The combination of these two items when placed near the body will relieve pain on a more accelerated basis than standard light therapy device.

BACKGROUND

Description of Prior Art

Pain relief has long been known to be a challenge around the world. Many areas of medicine are using chemicals and a diversity of electrical impulse devices. Recent information confirms that some electro-biomedical devices actually destroy nearby nerves while relief of pain is observed. Some others use lasers which are noted to destroy the tertiary cell structure. Opioids are now too dangerous and addictive.

We have seen many light therapy devices attempted in the last few decades which have had an impact on pain relief world-wide but each has its specific limitations or deficiencies.

Red light therapy has been identified to be used previously to some degree in accelerated healing of tissue and pain relief. Green light therapy is used in sleep disorders and autism. Key areas of study in the military are related to improve cures of PSTD and PTSD. Blue light is used in oral related needs. In skin care, however, blue light has been shown to destroy hair follicles thereby retarding hair growth.

Prior art devices function off of electrical impulses or penetrating the human body with extreme energy waves from a separate power source.

SUMMARY

The present invention functions in harmony with the human body.

The basic layer combination (copper tape, PVDF, and polarized film) is a very flexible item with numerous potential uses in medical care. It can be embedded as a laminated or cloth enclosed item into any and all variation of wraps or wellness products. It can also have a significant polymer base for each component which will reduce costs and potentially also lessen weight.

A quick description of options will be discussed here for pain relief in areas of the wrist, elbow, knee, arm, shoulder, chest, fingers, headaches and other sources of inflammatory pain. Also, the present invention can be helpful to relieve pain from, for example, arthritis, back pain, burns, bursitis, bites, broken bones, chest pain, cramps, cuts, depression, fibromyalgia, headaches, hiccups, heel spurs, hot flashes, heart palpitation, joint pain, kidney stone pain, menstrual pain, muscles aches, migraines, neuropathy, post-surgery sores, sore throat, sinus pain, scoliosis, shoulder pain, stiff neck, sprains, stitches, tattoo pain, tooth aches, tremors, ear aches, and pain from various foot ailments (including arthritis). As best as it is currently understood, the invention relieves inflammatory pain on at least a temporary basis.

Improvements have also been found in the area of peripheral neuralgia, varicose vein pain, ecchymosis, Reynaud phenomena, skin disorders, heart health, brain health and TMJ. Immediate micro-circulation and micro-current has been found to occur.

In many cases a piece of the basic layer combination placed on Scotch® Reusable pads can be used to best position the basic layer combination before the person's wrap is placed on the body.

A custom designed wrap will embed the invention layer as described below. Products can also be disposed in a belt form for other major pain relief needs for back pain, menstrual cramps, and neck and/or shoulder discomfort.

Other methods of providing convenience and ease of use have been described below. The invention may be in the form of a simple keychain adaptation or as a flexible cloth, to be used in areas such as sinuses or tooth pain relief on the side of the face or lower jaw area. An effective adaptation of the basic layers is to be able to aid in relieving pain in the feet, helping any discomfort which may bother the individual in that area of pain with a simple adaptation of the invention layer in a secured form. This can be used under any shoe insert, insoles or orthotics, either beneath a sole, between the foot (or a sock) and the sole, within a sock, or even attached to the outside of the shoe. An extremely thin invention basic layer (such as approximately 16 mil thickness) can be used.

A clip and string can be added to the card with the basic layer for safe keeping when not in use.

Direct skin contact is not necessary, but with the device of the present invention, no adverse effects have been noted to date with direct skin or elevated within an active range elevated from the skin.

The invention uses the basic layers as a resonator of the ultra-low reverberation of the body tissue energy. An improved light therapy device can be provided as the basic layers deflect an LED source at obscure angles. The tripolymer basic layers combination (polarizer, PVDF-film and copper tape) have obtained faster pain relief in projecting LED bulbs in a close field proximity, as an accelerator for LED light therapy.

The energy from the LED bulbs project at obscure angles towards the body, offering better treatment. The cellular frequency projected to the PVDF film and back is now penetrating deeper by the frequency of the LED bulbs and able to obtain stable and safe inflammatory pain relief quickly.

The LED bulbs are combined in a way that they complement the basic layers to help pain relief. Best utilization of the LED and the materials in the basic tri-layer combination having a polymeric foundation cause a very positive reaction on the body cellular and pain relief mechanisms.

BRIEF DESCRIPTION OF THE DRAWINGS

Advantages of the present invention will be readily appreciated as the same becomes better understood by reference to the following detailed description when considered in connection with the accompanying drawings wherein:

FIG. 1 is an exploded perspective schematic view of a product having the layers indicated in combination;

FIG. 2 is an exploded perspective schematic view of an alternate version of the product of FIG. 1;

FIGS. 3A and 3B illustrate sports tape incorporating the invention to be placed and adhered as needed or desired on a body;

FIG. 3C illustrates a credit card shaped product disposed into a sleeve;

FIGS. 3D, and 3E illustrate the use of the invention to relieve foot pain and disposed attached to the outside of a shoe or inserted into the inside of the shoe or underneath the insole of a shoe;

FIGS. 6A, 6B, 6C, 6D, 6E, 6F, 6G, 6H, and 6I illustrate the use of the invention in various applications to be positioned relatively to a person's body;

FIG. 15 illustrates a further combination of the invention where the LED is surrounded by the basic fil layers and has an elongated attachment for use as described below.

DETAILED DESCRIPTION

Figure 2A:
FIG. 2A is a cross-sectional view of the product of FIG. 2 along the line 2A-2A of FIG. 2.

Most relevant advantages of the invention are that it is non-invasive (below the skin) and drug-free (not ingested). Some of the other advantages have been previously mentioned above.

A major advantage is that the basic layers disclosed below can improve any product in the market today. It can be packaged to meet any configuration with LED devices.

The combined elements (LED bulbs and the basic layers) may also be incorporated into other wellness products to help accelerate relief or healing.

The copper tape layer acts as a reflective shield against loss of film activity away from the intended area of treatment, and can have a polymeric base to lower costs and lessen weight. Copper and silver are both noble metals which both have an extra electron in the outer orbit, thus causing e-spin/plasmon resonance. The latter is the cause of resonance with the human cell structure and mechanism. Other noble metals can also be used, but tend to be more expensive and, in normal cases, currently cost-prohibitive at this time.

One of the tri-layers used in the preferred embodiment of this invention is silver doped PVDF, again a polymeric foundation.

The third item in this tri-layer is a polarizer to make the field of frequency more effective and focused when being used near the body, again with a potentially polymeric foundation.

The total sealing of the tri-layer is a benefit in using it any way necessary or combined in any structure as required. As shown previously, no metallic covering is to be used. The covering in the preferred embodiment should be less than 1/16th inch thick. During the total process where the tri-layer is used, the temperature should not exceed 130 degrees F. Once this item is completed it is placed in close proximity to the LED bulbs.

The PVDF layer is a particularly effective material when used in the invention. Its proximity to the LED bulbs is also believed to be significant when used in that combination with any light therapy device. Both the PVDF and the LED bulbs have functional properties as related to cellular body tissue. The PVDF film is very significant due to its functional properties as related to cellular body tissue.

These properties are as follows:

Frequency: 1-2 Hertz.

Acoustic impedance is the same as human tissue. The physical nature is that it is hydrophobic (stabilizing thermodynamics of nearby $H_2O$ molecules) a generator of entropy. The basic nature of PVDF is the sensitivity to low energy changes. i.e. pressure, temperature, vibration and very low level disturbances.

The unique function of PVDF makes it suitable for the purpose of pain relief and possibly long term relief.

The nature of the LED's is that they are a standard configured bulb in Red, Green or Blue. Each designates a clearly defined frequency of energy. Also Purple bulbs (near-UV) can have certain applications.

The unique function of the PVDF film makes it suitable for the purpose of pain relief and possibly long-term relief.

If skin contact is available, it is probably best to do so, but not believed to be necessarily required. The field of effect is a range from approximately ¾" to 1" at one end and zero at the other end of the range, which meets the requirement for positive results. The LED bulbs will further penetrate up to 2" in depth in providing energy to all nearby cells.

Using the device through clothing is fine, but not as quick in elapsed time to result in pain relief in a designated area.

In non-clinical trials, all of the above methods/products of the present invention were conclusive with positive results.

Based on all the results of our trials it is best stated in the following statement. In general application of the invention to cause pain relief, our belief is that the PVDF film acts in similar reflective fashion as one would use radar and/or a mirror. Some information as to this possibility can be seen in time-reversal signaling. With interaction with or without the LED bulbs the invention is believed to be very effective for pain relief.

This is an observation due to results when the invention is used near the body. Cellular frequencies projected from the body are activating the PVDF film as a sponge. With its high sensitivity it becomes more active, thus projecting this newly focused energy back into the body. The frequencies at play are positive energy from the body, therefore more positive energy is reflected back for absorption by the cell.

The frequencies exchanged in this manner signal the cells which are in distress, that there is new energy available to regenerate itself and not be a source of pain.

Based on Dr. K. Meyl (THE NEW TESLA) in his analysis of the new physics, he proves the energy fields transmitted in nature are scalar waves/vortices. He also proves in biology that this type of energy/frequency is the fundamental basis of cellular communication. Scalar waves are a combination of electrical energy and electromagnetic wave propagation.

In the disclosure of the invention here, in some embodiments light energy is added to this affect by using LED bulbs as such an energy source external to the body.

This new area of scientific study of LED bulb energy generally is being proven more and more worldwide today. It is believed that the total functionality of the PVDF film in the invention is now added to this new area of science, which along with LED light therapy cuts the treatment time by about ⅕ to ¹⁄₁₀th. In this way we can also now understand better why it is so effective in relation to human tissue regeneration and to help relieve pain.

FIGS. 1 through 5 are included in U.S. Patent Application No. and the description is incorporated into this application. The layers described in that application are the "basic layers" as that term is used in throughout this application. The use of the basic layers with an LED light source.

The top and bottom covers can be of any material other than metallic in composition. The invention can be surrounded by laminating or bound in two pieces of sports tape. It may also be incorporated into other wellness products to help accelerate relief or healing.

The copper tape acts as a reflective shield against loss of film activity away from the body. Copper is also an enhancement to the invention in that it is also a generator of resonance.

Copper and silver are both noble metals which both have an extra electron in the outer orbit, thus e-spin/plasmon resonance exists. The latter is the cause of resonance with the body.

The PVDF used in this invention is preferably silver doped.

The polarizer polymer is used to make this resonance more effective when being used.

The total sealing of the copper tape/PVDF film/polarizer become one integrated item. As previously shown the coverings may be made of any material other than metallic materials. The coverings must be less than ¹⁄₁₆th inch thick. During the process of sealing the temperature must not exceed 130 degrees F. It is preferred that the covering is flexible to conform against the surface of the body to which it is applied, although some stiffness in the credit card sized package is manageable for use in relief of headaches and other inflammatory pain.

When the invention is used near the body, cellular frequencies are projected out and PVDF film with high sensitivity becomes more active, thus causing positive frequency feedback. The frequencies exchanged in this manner signal to the cells which are in dysfunction that there is new energy available to regenerate themselves.

Once the three components copper tape 10 (¾"×2" as shown), polarizer 12 (⅓"×1¾" as shown), and PVDF film 14 (⅓"×1¾" as shown) are bound together as ITEM A, it may be used in a number of different ways as demonstrated in the following pictures. For all the samples the ITEM A has been ghosted. In actual use the ITEM A is preferred to be enclosed without visual detection such as the cover or enclosure in FIG. 1 which would be non-metallic and have the cover portions 16 and 18 heat sealed or otherwise bonded together.

If the polarizer 12 is disposed on only one side of PVDF film 14, then there will be directionality to the device wherein the side of the device having the polarizer would be the side that would face the body (toward the skin) as set forth in FIG. 1 and the B (body) side. Such directionality would be noted on the packaging for the device to explain to the user that one side of the device faces the body (or skin) and the other side faces away from the body (or skin). It is also anticipated that the device may be manufactured with a PVDF film and polarizer combination on both sides of a copper strip, which would eliminate any need for directionality.

An alternative to ITEM A would be ITEM B as shown in FIGS. 2 and 2A. A strip of PVDF film is dipped on both sides into a bath of polyvinyl alcohol combined with iodine (to cause a polarizing effect) as a polarizing layer 21 and 23 on both sides of the PVDF film 14. Then the PVDF is sprayed with conductive copper to create a layer on both sides 20 and 22 to eliminate the copper tape 10 of ITEM A to create ITEM B. The assembly of the packaging and handling is made that much easier with the combined ITEM B device. Also, ITEM B would not have such a directionality issue, and would work effectively in either direction (on either side) as applied to the body. ITEM B, however, could be sprayed on one side only and provide the same benefits as ITEM A but be directional.

Figure 2B:
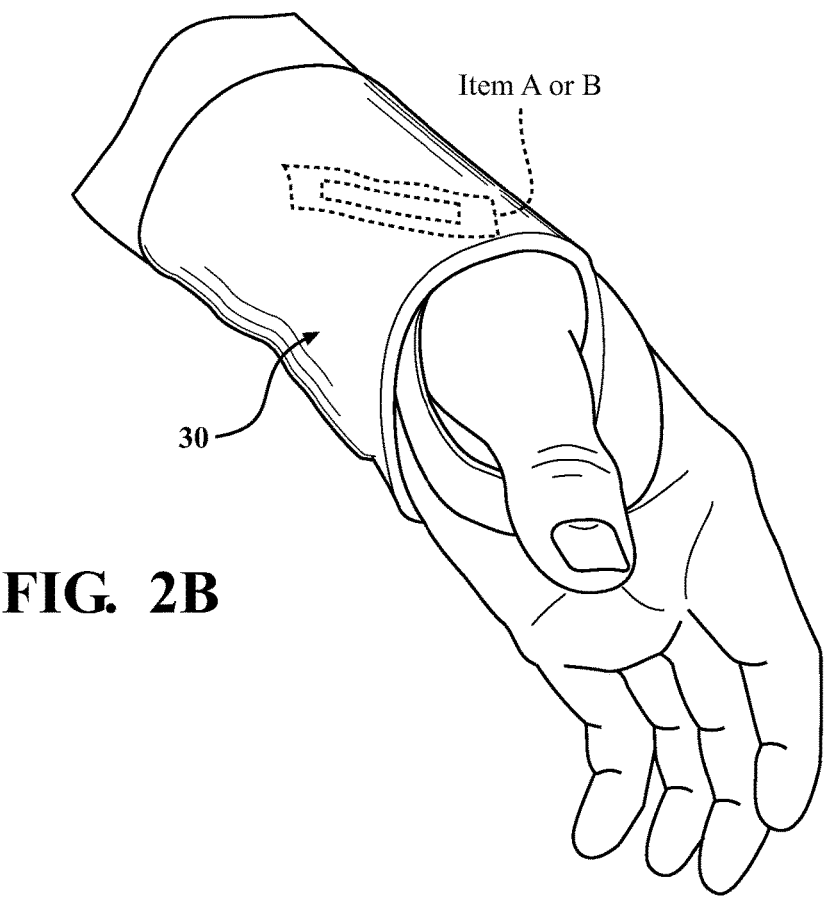
FIGS. 2B, 2C, and 2D illustrate packaging using the invention packaged into a wrist brace, an elbow brace, and a knee brace, respectively.
Figure 2C:
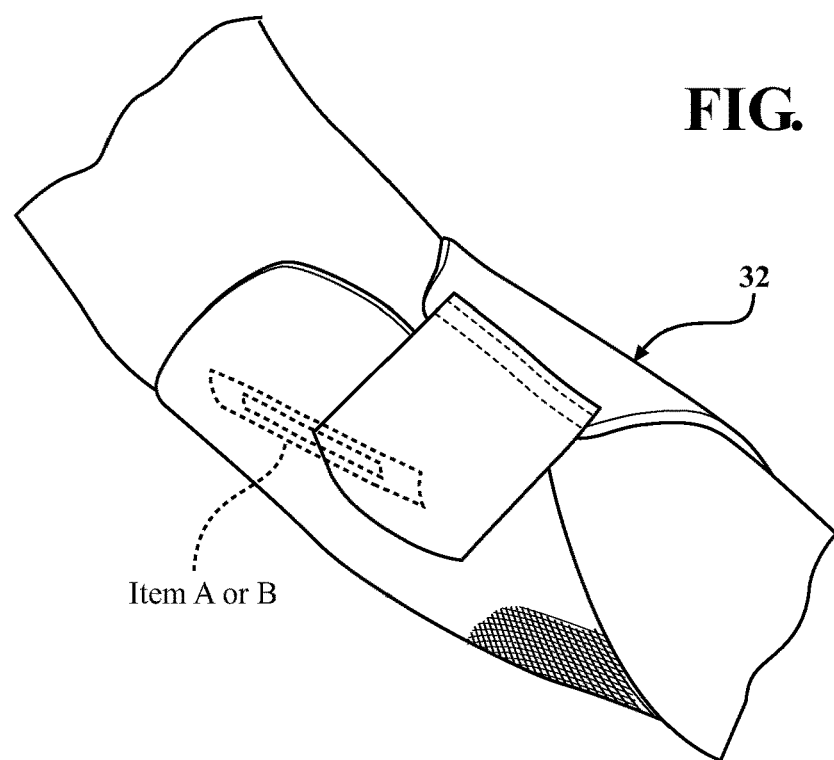
Figure 2D:
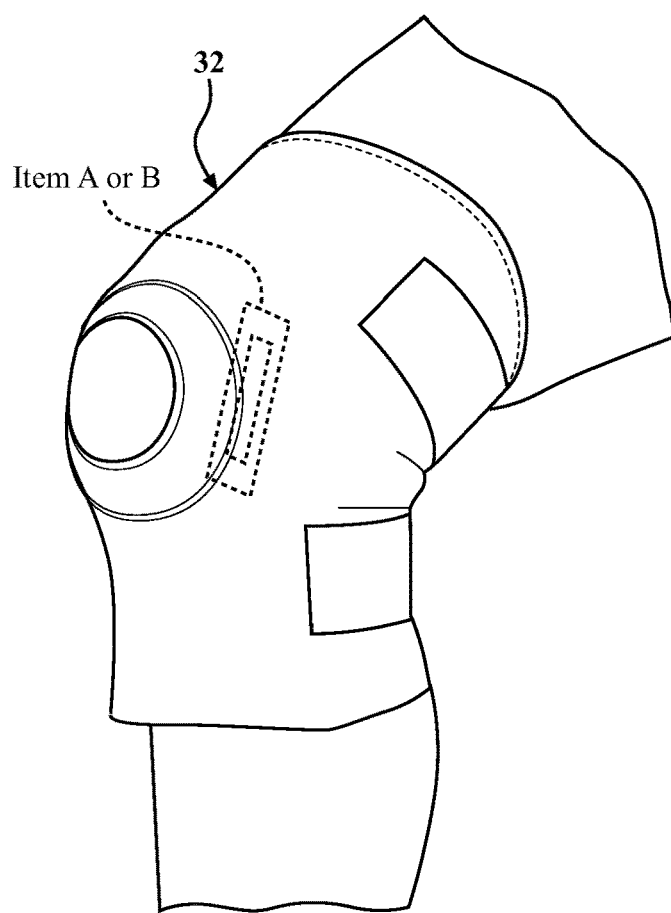

FIGS. 2B. 2C, and 2D demonstrate the application of invention with existing wrist joint wrap 30, elbow joint wrap 32 and knee joint wrap 34. In these images the ITEM A or ITEM B is ghosted and preferably between the wrap and the skin in contact with the skin, but it is not necessary to make contact with the skin, but may be attached on the outside of wrap as deemed necessary (via Velcro packaging, sports tape or some like functional attachment). Based on analysis to date, it is understood that the effectiveness of the invention in this form can occur in a range from at least one-half inch from the outer skin of the body up to contact with the body and through porous material such as a wrap. It is not limited to joints, but, in fact, is believed to be effective in response to any inflammatory pain that the body would express where the acoustic impedance of the device is the same as human tissue (or nerves) that emanate from inflammatory pain. A wrap in the forearm for tennis elbow, a thigh wrap, a calf wrap, an ankle brace, a back wrap, and a myriad of other options exist for placement of the invention on the pain site or at a meridian (as defined in acupuncture and similar disciplines) controlling or otherwise impacting the pain site.

FIGS. 3A, 3B, 3C, 3D, and 3E demonstrate different configurations of said invention as packaged. Additional configurations are shown in FIGS. 6A, 6B, 6C, 6D, 6E, 6F, 6G, 6H, 6I, 11, 12A, 13, 14, and 15.

FIG. 3A demonstrates that ITEM A or B can be embedded on adhesive tape, such as sports tape 50. Once the ITEM A or ITEM B product is placed on the tape, the tape can then be placed on any part of the body where the pain emanates from, on any pain meridian that would normally be used for acupuncture therapy or even a combination thereof. Another option might be to place the ITEM A or B into the gauze of an adhesive bandage 52 as shown in FIG. 3B to place the invention in the desired location. The invention can also be used effectively with KT Tape such as that supplied by KT Health LLC and shown as 150 in FIG. 5 where ITEM A or ITEM B would be placed between the tape and the skin for specific placement at a source of inflammatory pain as determined by the person or therapist who defines the pain site and enhance whatever therapeutic advantages are supplied by the KT Tape itself.

FIG. 3C illustrates that the packaging can include a credit card sized outer layer 60 that could be transported in any sleeve 62 (or wallet) or other location accessible to a user. In this form, it is available to a user at all times. For example, if a user has a headache (migraine or otherwise), the user can take the credit card sized package 60 and apply it by hand to the forehead, back of the neck or other placement in order to obtain temporary pain relief for the headache, which many times also relieves the headache itself. This could be placed via tape or other mechanism to hold it in place. The place of application might also be to the cheek or other area around the mouth (outside of the skin) if there is dental pain that needs to be temporarily alleviated due to some dental incident or dental procedure. A user could also place the credit card sized device 60 within a carrier or package that might already exist near the pain site, such as the portion of a brassiere near the site of some back pain, or a portion of a belt or flexible portion of clothing near a pain site in the abdomen or lower back. Such activity could be used as an alternative to adhesive tape or other attachment devices.

Due to the fact that ITEM A or ITEM B is flexible, it can be used any wellness or therapeutic application where inflammatory pain is involved.

Following examples show our present configuration of ITEM A sealed in a laminate. FIG. 3C illustrates the invention in a credit card sized or smaller package 60 that can be placed in association within a shoe 70 to relieve inflammatory foot pain. The ITEM A or ITEM B can be attached to the outside of the shoe 70 (as shown in FIG. 3D) or can be placed anywhere as selected on the inside of the shoe 70. It may be placed between the shoe 70 and the shoe insole. It may be placed on the insole of the shoe 70 either fixed or loosely held in place by the foot (either with a sock on the foot or sockless).

With new location designs such as pocketing of ITEM A once sealed, we are looking at simple and convenient ways of using this invention.

Figure 3E:
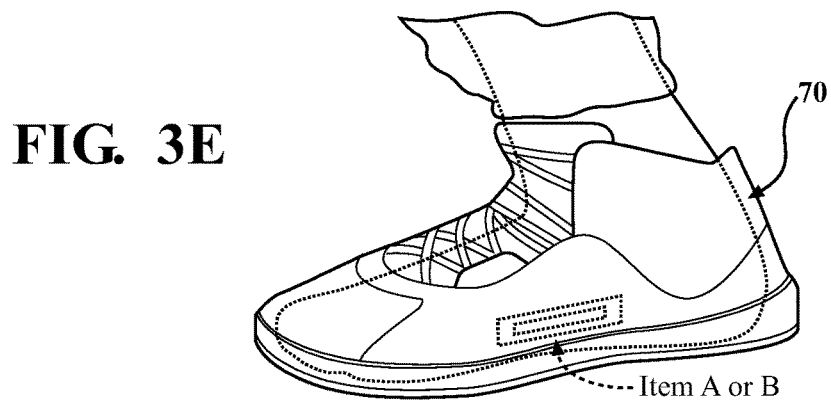

Additional designs include FIGS. 3D, and 3E to demonstrate different configurations of said invention as packaged. Additional configurations are shown in FIGS. 6A, 6B, 6C, 6D, 6E, 6F, 6G, 6H, 6I, 11, 12A, 13, 14, and 15.

Figure 6A:
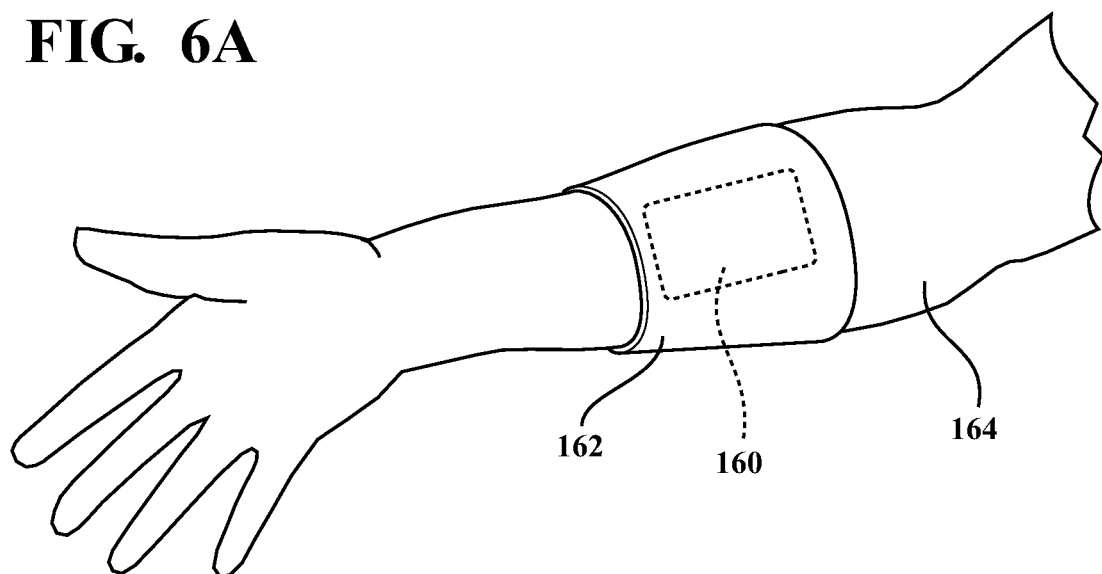
Figure 6B:
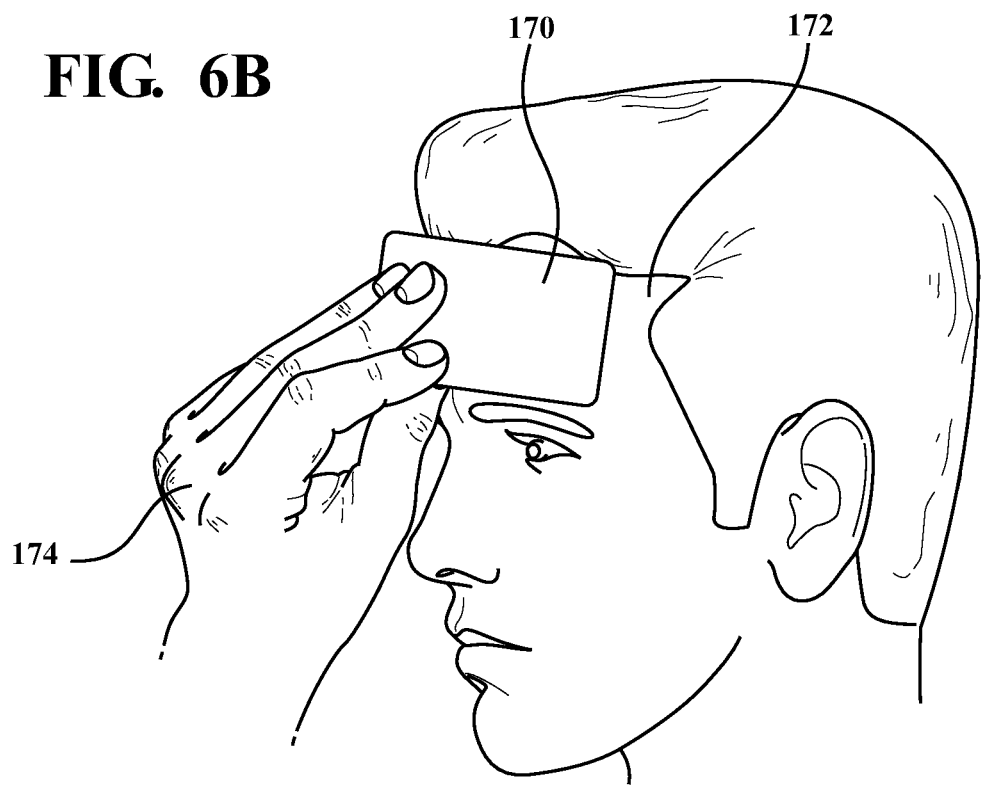

For example, the device 160 of FIG. 6A has ITEM A or ITEM B embedded in a wrap 162 and positioned to relieve the pain of tennis elbow or similar maladies on a human arm 164. In FIG. 6B, the device 170 (as ITEM A or ITEM B) is used for treatment of headaches, particularly migraine headaches, by the manual placement of the ITEM A or ITEM B device 170 at the location of the pain on the forehead 172 (or otherwise), or alternatively at the acupuncture pressure point that is associated with the location of the pain by hand 174 or alternatively by affixing the device 170 by adhesive tape, such as masking tape or other adhesive tape. FIG. 6D discloses the device 180 (ITEM A or ITEM B) located on the shoulder 182 to relieve shoulder pain with the placement location determination by the existing clothing in that area, such as a suspender 184 (as shown), a brassiere strap or the like, although it has been found that placement of a card in the form of ITEM A or ITEM B can be held even by a shirt if the wearer is not actively moving to dislodge the item.

Figure 6C:
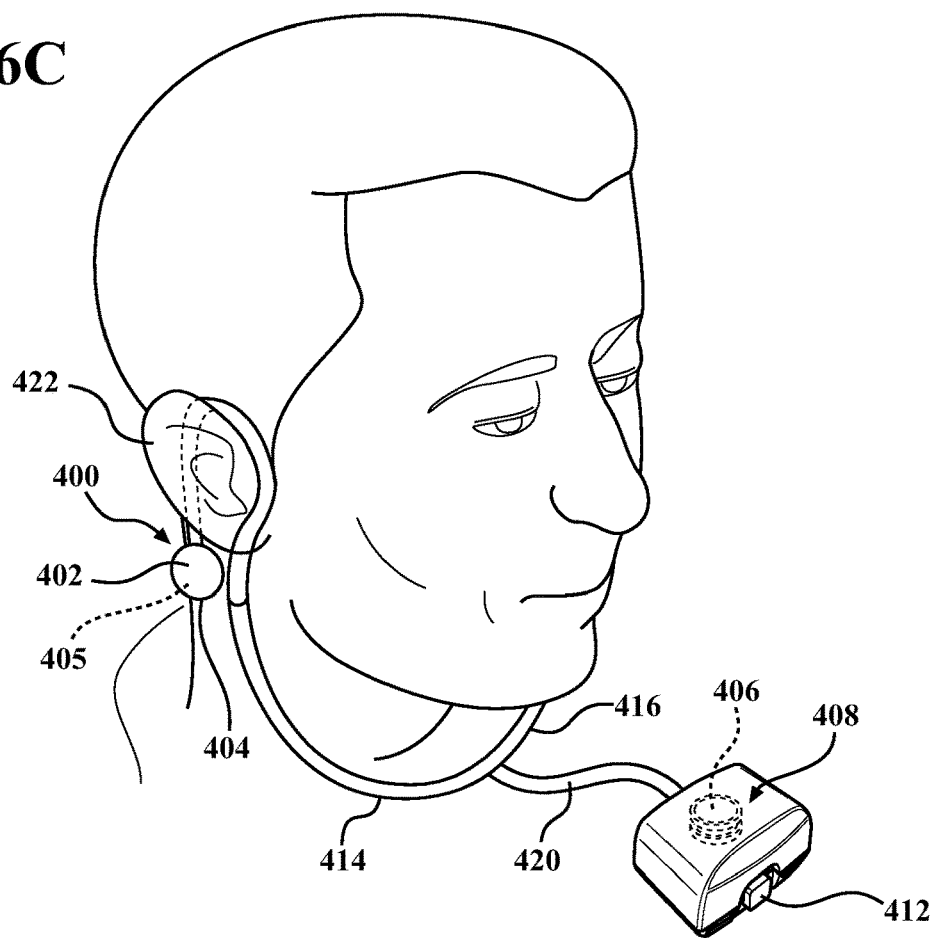
Figure 6D:
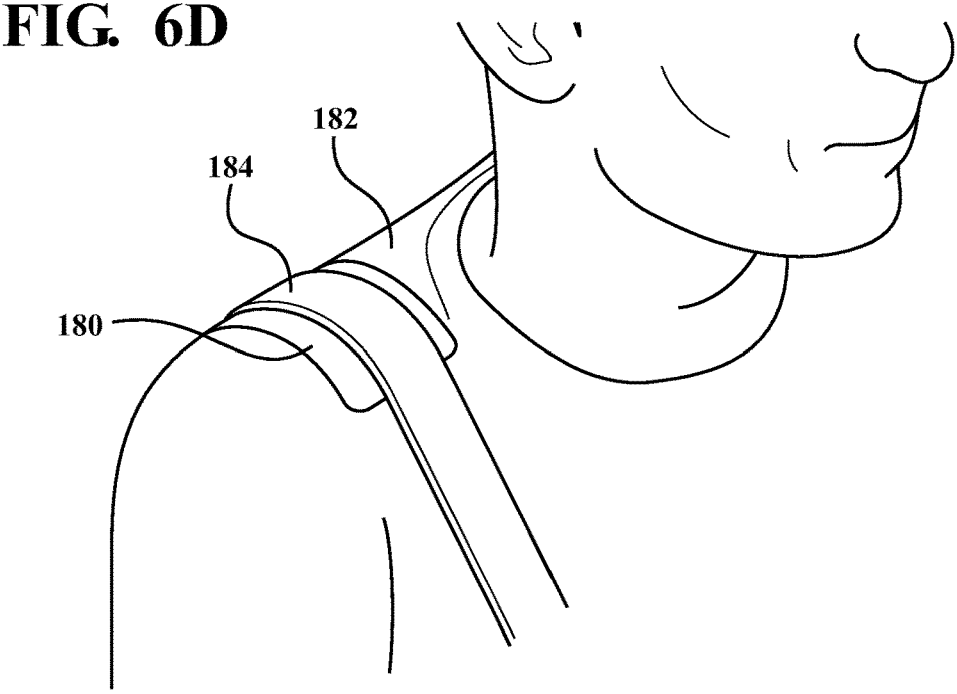
Figure 6E:
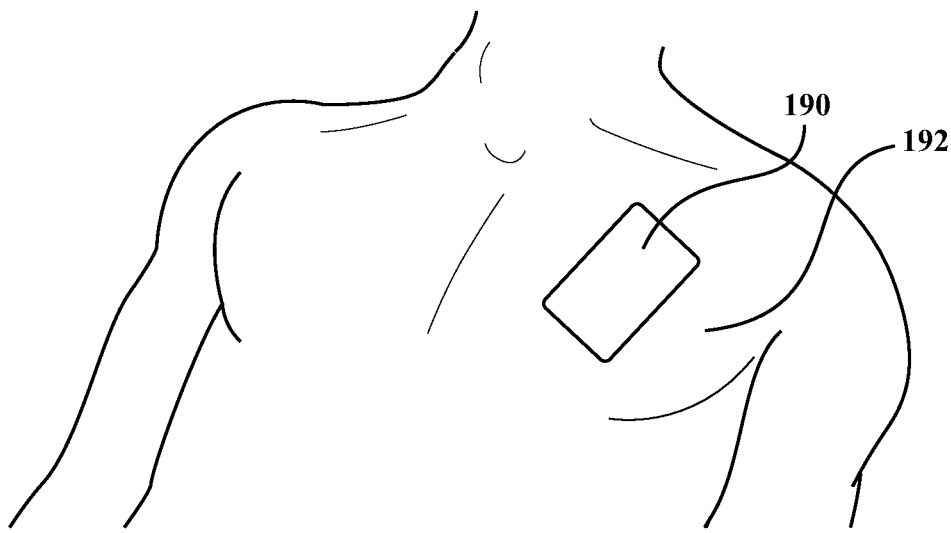
Figure 6F:
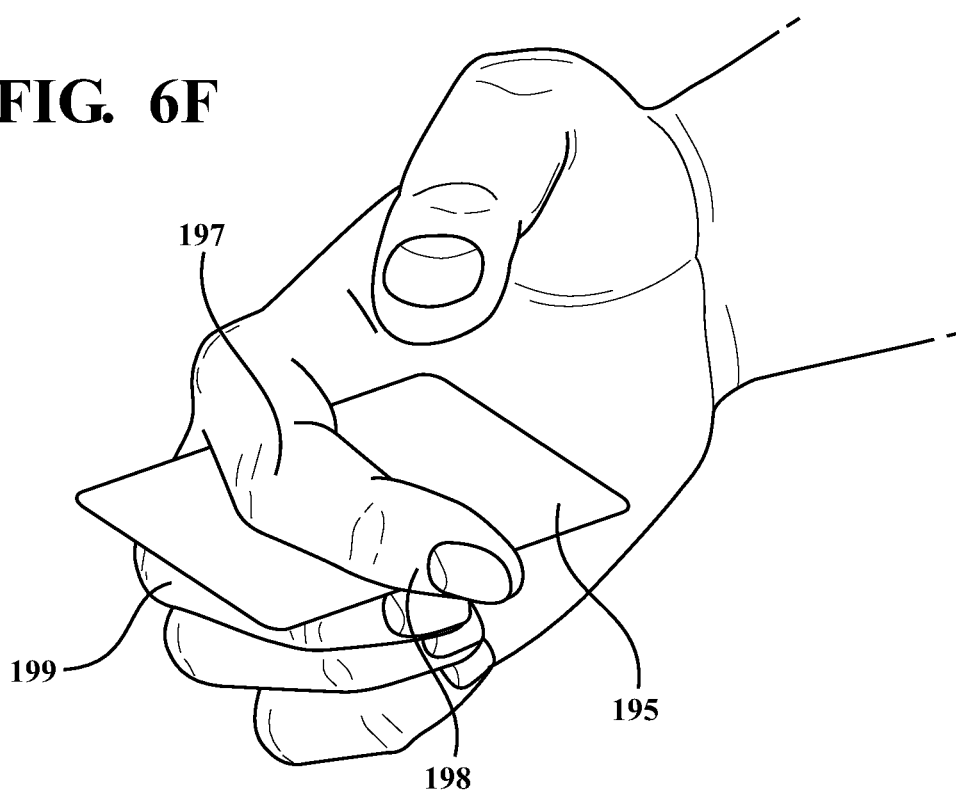

FIG. 6E indicates the use of a device 190 (ITEM A or ITEM B) on the chest 192 for muscle pain, or, in some cases, relief of inflammatory pain from other issues, such as those relating to heart ailments. FIG. 6F illustrates the use of the device 195 (ITEM A or ITEM B) can be as simple as holding the device 195 against a knuckle 197, a finger 198 or 199, or other source of inflammatory pain to resolve the pain at least on a temporary basis.

Figure 6I:
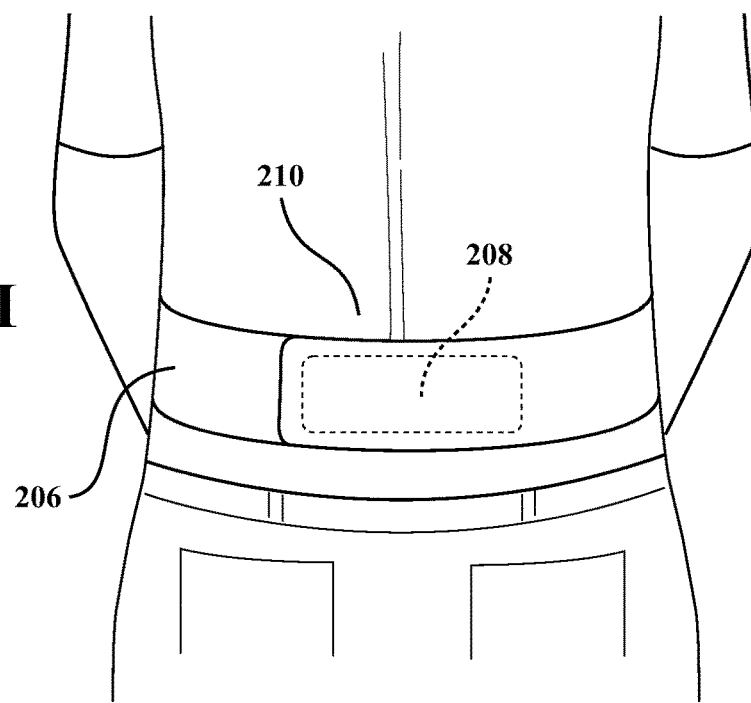

FIGS. 6H and 6I illustrate the use of the device 200 (ITEM A or ITEM B) embedded in a belt or other wrap 202 around the waistline 204 of a human body. The belt or wrap 202 can be a Velcro attached expandable stretch wrap or even a standard non-expandable belt as desired. In FIG. 6H, the belt or wrap 202 has a strip of the device 200 (ITEM A or ITEM B) extending preferably for approximately eleven inches, and is used to treat the inflammatory pain of menstrual cramps and the like with the placement of the device 200 at the front of the body. In FIG. 6I, the wrap 206 is used against the back 210 of a human body to relieve inflammatory pain from any muscular or skeletal issue in that area.

The device can also improve current items which entail wellness healing.

Figure 4:
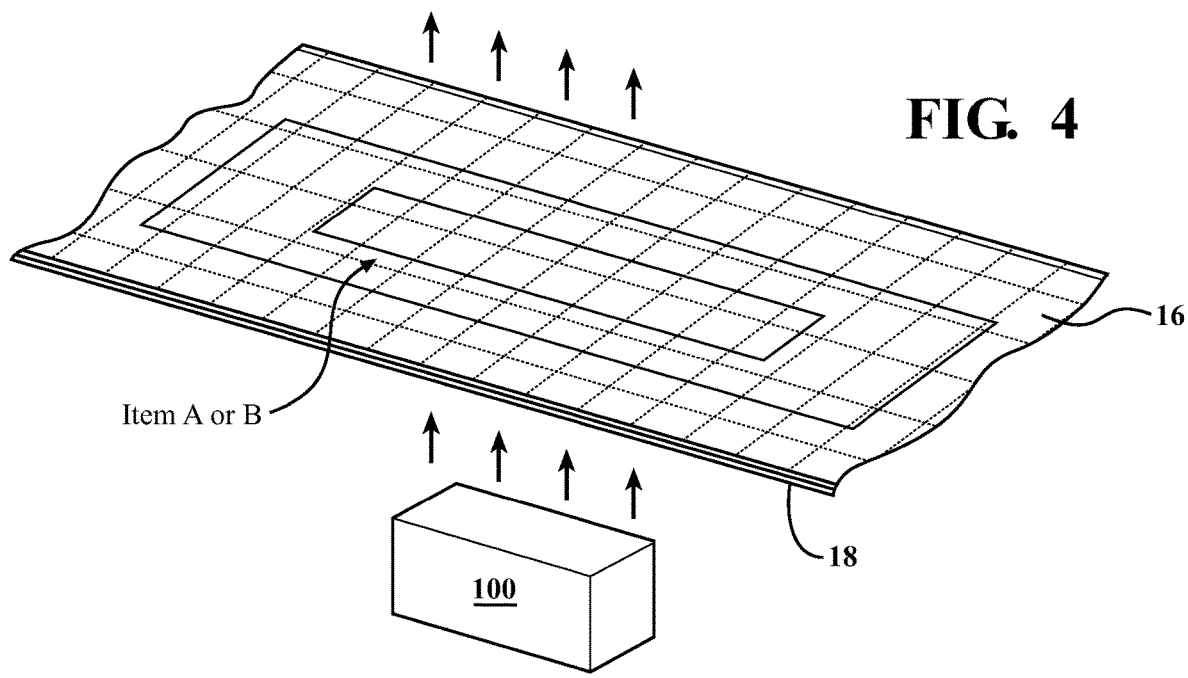
FIG. 4 illustrates the use of the invention with a light therapy device.
Figure 5:
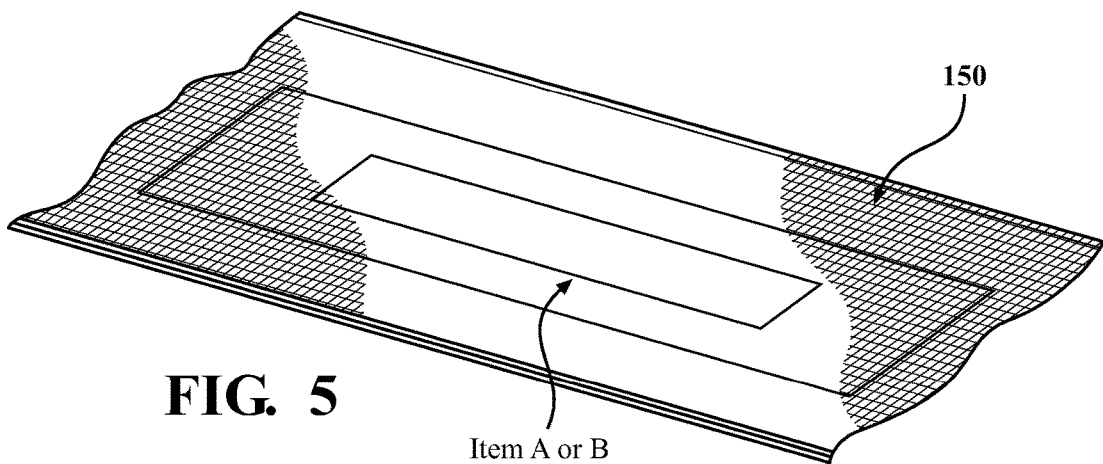
FIG. 5 illustrates another option where the invention is embedded in a KT Tape configuration.

As shown in FIG. 4, with a red laser light therapy product 100, the device of the present invention is able to cut usage times required by manufacturers of red laser therapy devices (pulsed or non-pulsed) down by at least half the amount of time. Half the time is required with ITEM A or ITEM B embedded into or otherwise attached to the light therapy device where the laser is directed through the ITEM A or ITEM B as shown in FIG. 5, where 100 is the source of the laser and the arrows demonstrate the direction of treatment toward the body (or skin). As described here, the ITEM A or ITEM B can be placed in between the red laser light source and the body however the user determines it to be packaged as long as the laser light runs through ITEM A or ITEM B prior to reaching the body (or skin).

In using this invention the time required near body application are as follows: For headaches approximately 30-60 seconds. Other aches use in inflammatory pain area for about 2-5 minutes. More severe inflammatory pain may take 20 to 30 minutes. For continuous use, 6-8 hours may relieve severe pain within this time frame.

Figure 7A:
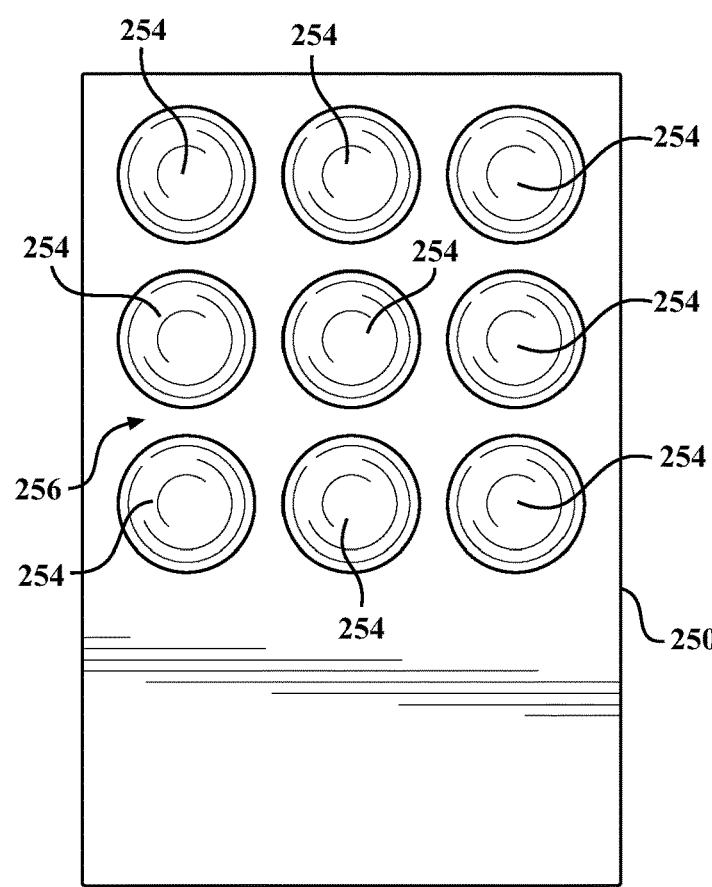
FIGS. 7A and 7B illustrate the use of the invention with a light array.
Figure 7C:
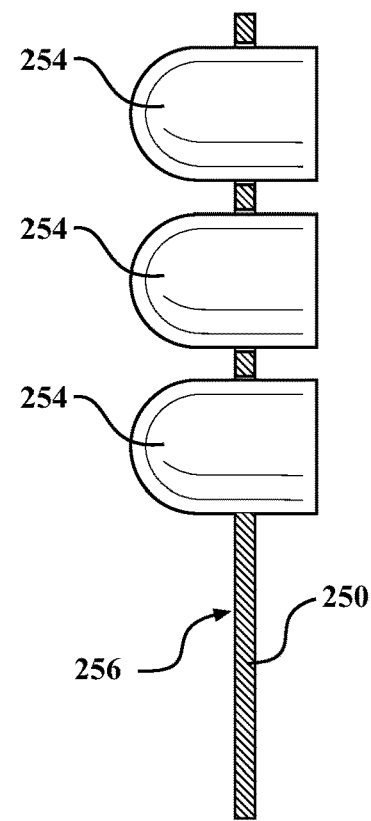
FIG. 7C illustrates a side view of FIG. 7A.

FIG. 7A illustrates the use of the basic layers 250 with an array 252 of LED bulbs 254. The array 252 can include a variety of external packaging, but it would be preferable to have a transparent plastic covering as described in other embodiments of this invention here along with a battery power source and switching mechanism to engage the power. The basic layers 250 (ITEM A or ITEM B) can be honeycombed around the array 252 within the packaging at an intermediate point in the LED bulbs 254 as shown in FIG. 7C to form a lattice 256 around the LED bulbs 254.

Figure 7B:
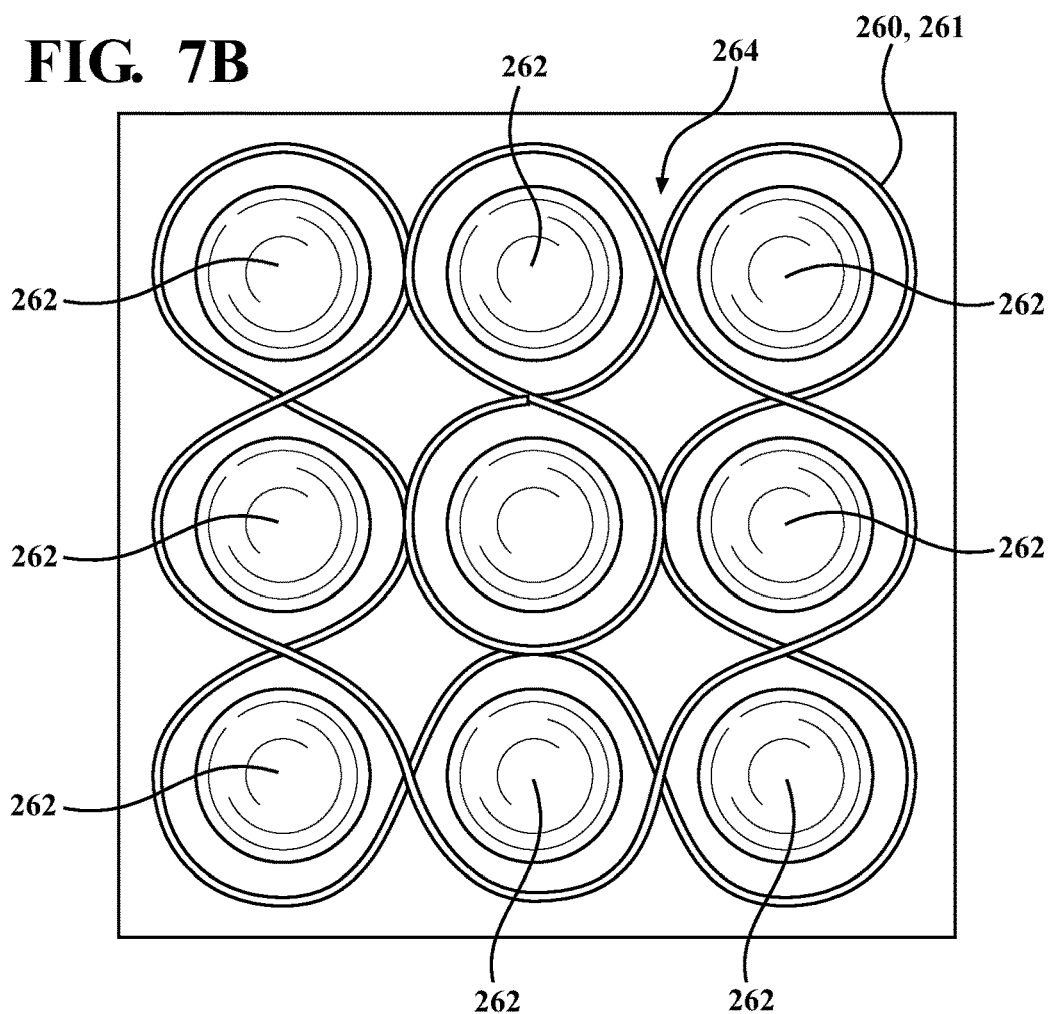

FIG. 7B discloses an alternate version of FIG. 7A where the basic layer 260 is configured as a wire and wrapped around LED bulbs 262 in an array 264 to still establish close proximity as frequency binding for pain relief. Again this would be packaged in a transparent or translucent hard case along with a battery power source and switching mechanism to engage the power.

Figure 8A:
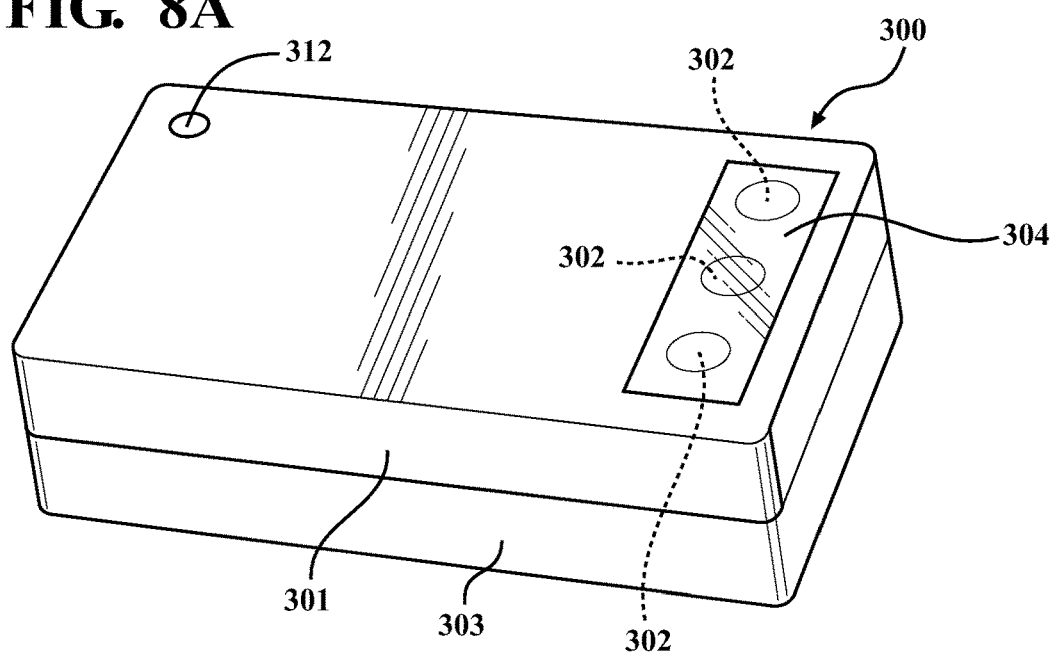
FIGS. 8A, 8B, 8C, 8D, 8E, 8F, 8G, and 8H illustrate a light therapy product or parts thereof with an integrated layer to provide an integrated light therapy invention.
Figure 8B:
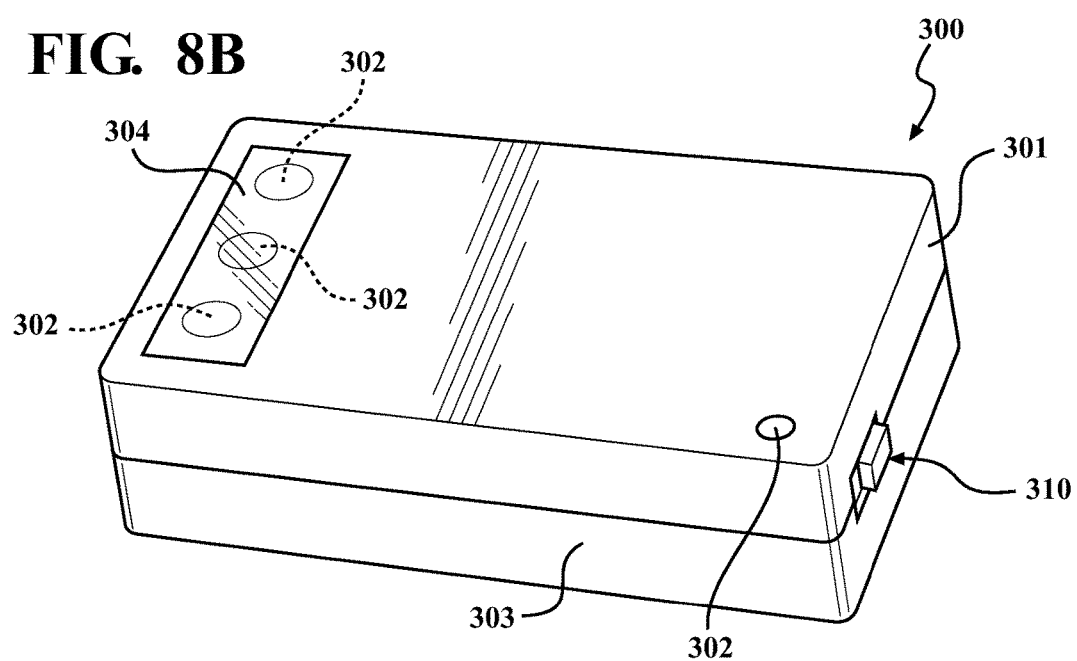

FIG. 8A, as an elevated perspective view, shows a basic and simple configuration of one embodiment of an accelerated light therapy device 300 of the present invention. LED bulbs 302 (preferably Red, but may be Green or Blue in certain circumstances) are shown in an array 308 through a light window 304 within a two piece case 301 and 303. FIG. 8B is a reversed elevated perspective view of FIG. 8A to show the on/off switch 310 or the positioning of a similar control. Case access may be made via an access hole 312, which may also aid in the separation of the top 301 and bottom 303 for service, such as replacement of the LED bulbs 302 or power source/battery 315 which is conventionally wired to the bulbs 302 via the array 308.

Figure 8C:
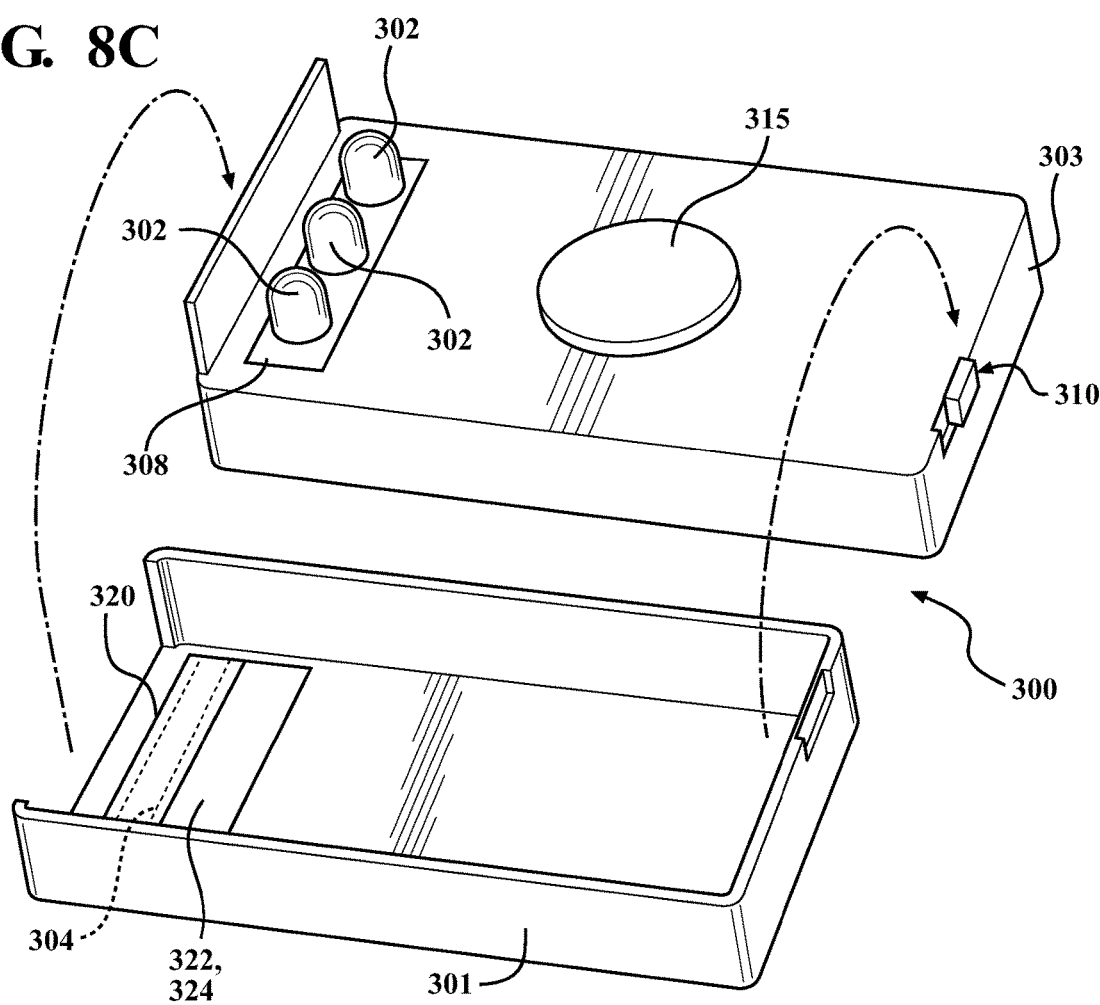
Figure 8D:
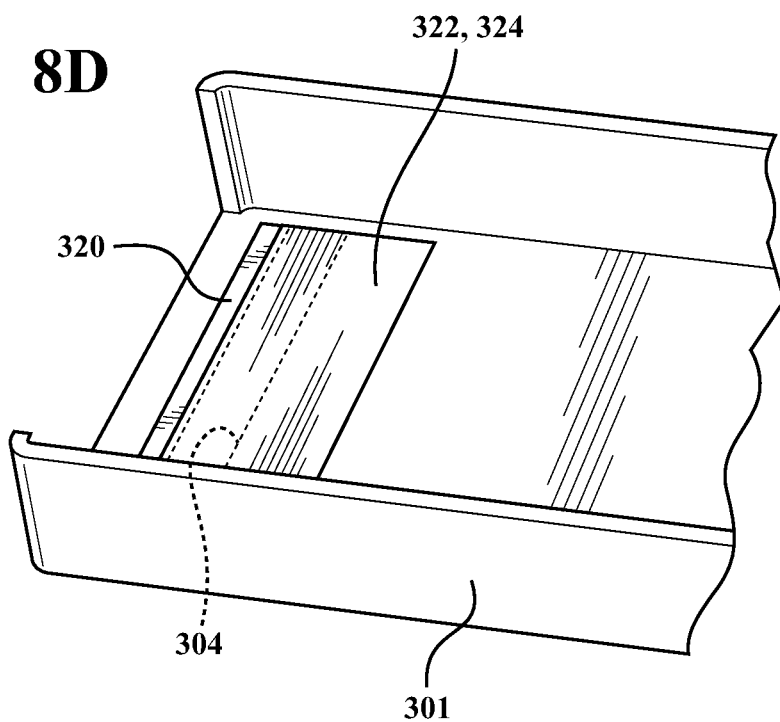
Figure 8E:
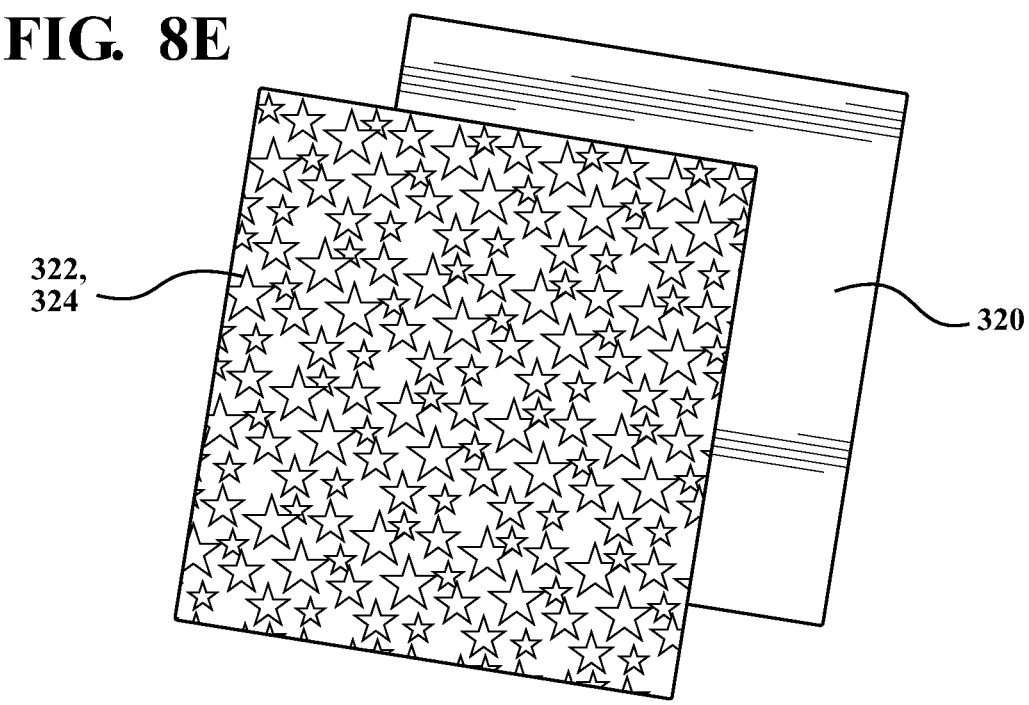
Figure 8F:
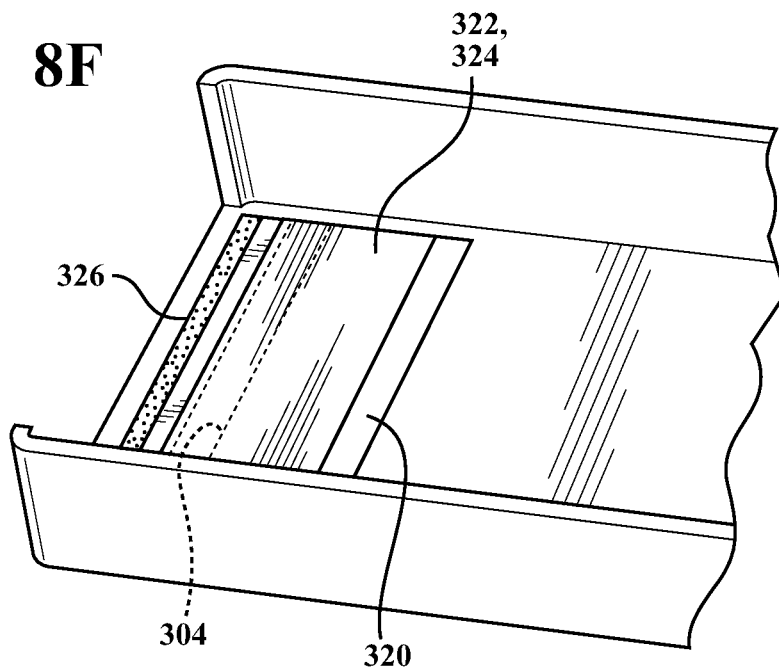

In FIG. 8C the internal items and positions of items are shown within the casing 301, 303 of the device 300. FIG. 8A, 8B, or 8C can include one to three LED bulbs 302 as the source of light therapy, in combination with the basic tri-layer in association with the LED bulbs 302. The bulbs 302 preferably are sprayed with a Spray Diffuser (such as Frosted Glass Spray Paint by RUST-OLEUM®). As shown in FIG. 8D, there is a clear window 304 with only the polarizer 320 in the direct path of the LED bulbs 302. The other two layers 322, 324 (PVDF layer as described above in either a PVDF combination with copper tape or sprayed with a polymer based copper layer (such as KRYLON® Copper Spray Paint)) is set adjacent the window 304 and has been found to energize the LED bulbs 302 as well as reflect any inflammatory pain it encounters. The power source is a three volt coin shaped battery 315 wired to the bulbs 302 in a conventional manner. The LED bulbs 302 energy partners with the plasmon resonance of the tri-layer 320, 322, 324 to accelerate the projection and impact on the body.

In FIG. 8D, the LED bulbs 302 and the window 304 are covered by the full tri-layer with the polarizer layer 320 facing the body while the device 300 is in use, then the PVDF layer 322—is disposed (preferably coated as a polymer/copper layer 324 on at least one side of the PVDF layer 322 with the KRYLON® Copper Spray Paint) as the next layers away from the body as the device 300 is in use, and then the LED bulbs 302 as shown. In this case the light energizes the layers 320, 322, 324 which, in turn, generates more energy to be projected to cells. The LED bulbs 302 have all three layers between the LED bulbs 302 and the window 304 as shown schematically in FIG. 9. FIG. 8 also indicates the general location 330 of the LED bulbs 302 and the layers 320, 322, 324 in a side view of the device.

Figure 8G:
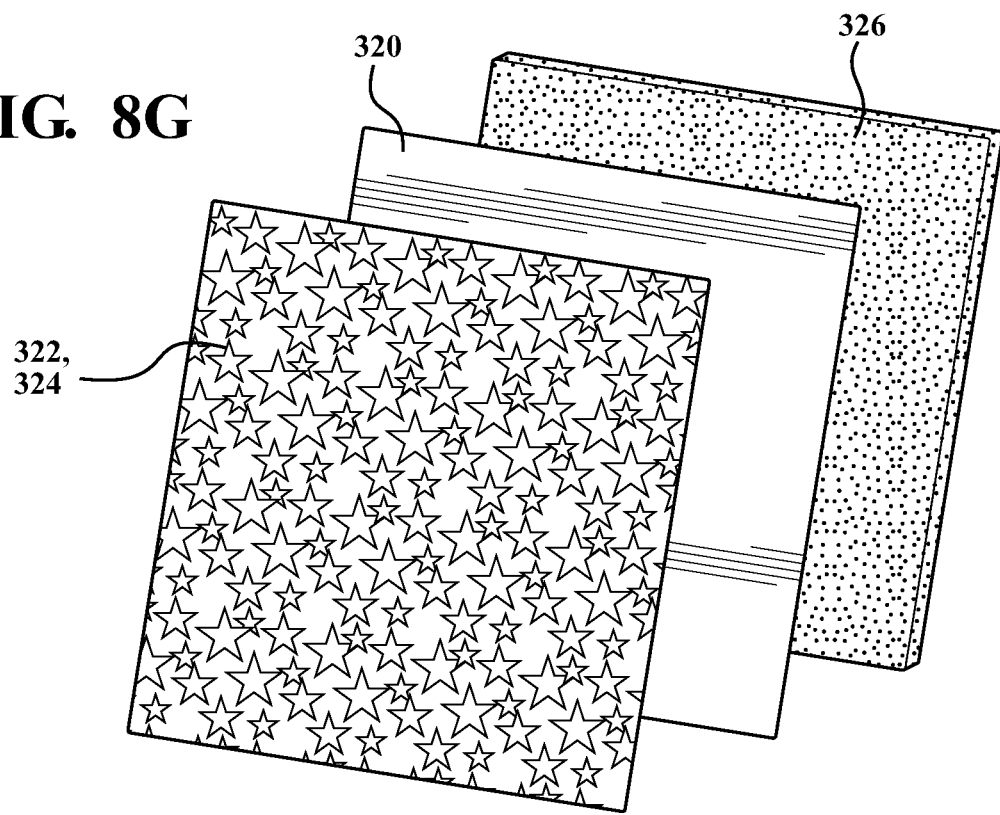
Figure 8H:
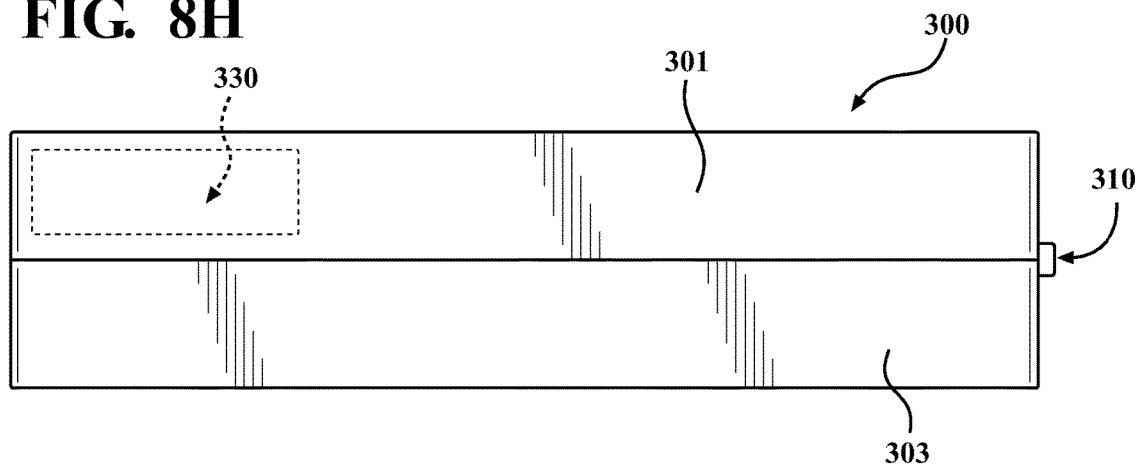
Figure 9:
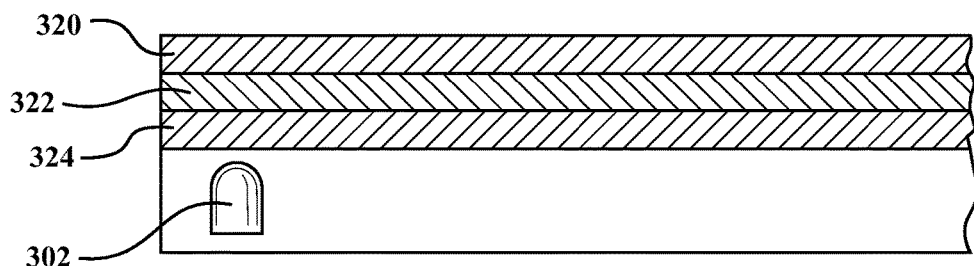
FIGS. 9 and 10 illustrate alternative layers for the invention.
Figure 10:
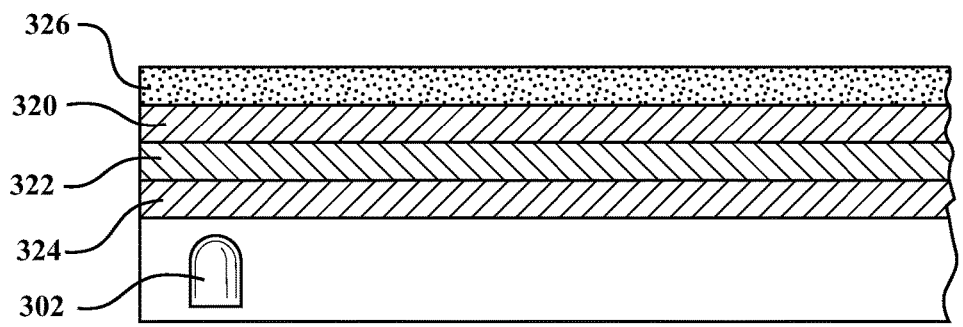

FIG. 8G (along with FIG. 10) offers another alternative taking a more elapsed time consuming method in providing light therapy. By using a water filter 326 as the layer between the body and the layers 320, 322, 324 (toward the body when in use), a slower field of resonance occurs, which can be desired in certain situations. FIG. 8G shows the placement of the layers used in this embodiment of the invention but with a filter component as an additional layer to control the amount of energy flowing into the body. The polarizer film 320 is approximately 12 mil in thickness and an area of 1 and ½" square. The PVDF film 322 is approximately same size, but only 28 um in thickness. It is coated with the copper spray paint on one side as shown schematically in FIG. 10, but could be painted on both sides or replaced with a copper tape about 3 mil in thickness to measure out at about same area as the other layers. The water filter 326 has a variety of possibilities, but it is currently determined that it have a thickness less than or equal to the thinnest layer and held in a conventional manner with the casing 301 via a suitable container that would not permit leakage as shown schematically in FIG. 10. The LED bulbs 302 can be Red, Green or Blue.

FIG. 7A provides a simple method in high production and/or quick adaptation of the layers 250 (polarizer, PVDF, copper) to other wellness products. By using a lattice pattern 256 to have the LED bulbs 254 sit in the tri-layer lattice 256 would be in even plane with the LED bulbs 254, as shown in FIG. 7C. The lattice pattern 256 would sit at an intermediate position along the axis of each LED bulb 254. The lattice pattern 256 can alternatively be in the form of a honeycomb to further enhance/accelerate the capabilities of the device.

FIG. 7B demonstrates the use of PVDF wire 260 sprayed with a copper compound (KRYLON® Copper Paint Spray set in a polymeric base) to establish a second layer 261 on the wire 260. The PVDF wire 260 and second layer 261 are then wrapped around the LED bulbs 262 in an array 264, which would still establish close proximity as frequency binding for pain relief and create a lattice or honeycomb effect.

In FIG. 15, and as applied in FIGS. 6C and 6G, is a novel and hygienically safe device are shown as an external light therapy device for ear pain or Maneer's or similar afflictions (FIG. 6C), or an external (as shown) nasal/sinus pain light therapy device. The options available on the market which do not utilize the invention tend to be cumbersome and/or ineffective. As shown in FIG. 15, the end portion 400 comprises a pulsing LED bulb mechanism 402 surrounded by a layered film 404 of the present invention configured into a bulbous shape to surround the pulsing LED bulb 405 or bulb array. The mechanism 402 is attached to a power source 406, such as a 2-2032 battery in a casing 408, via an insulated wire 410. The power source would also have an on/off switch 412 or similar control. FIG. 6C illustrates such a mechanism 402 with two branches 414, 416 (one for each ear) controlled by a control box 418 via insulated wire 420. Each side or branch 414, 416 would have an end portion 400 of the layered film 404 to surround an LED bulb 405 or bulb array, so that it can be conveniently wrapped around each ear 422 to hold the end portions 400 in place, as well as place it in a therapeutically effective area, such as behind each ear 422 as shown. In FIG. 6G, the end portion 400 is placed at or near the area where it can relief nasal or sinus pain, such as that area shown in FIG. 6G. It is anticipated that such a device could be disposed internally into the nostril to relieve pain through mucous membranes, but effective pain relief has been found to be evident using the device as shown externally of the skin without entering the nostril.

Figure 11:
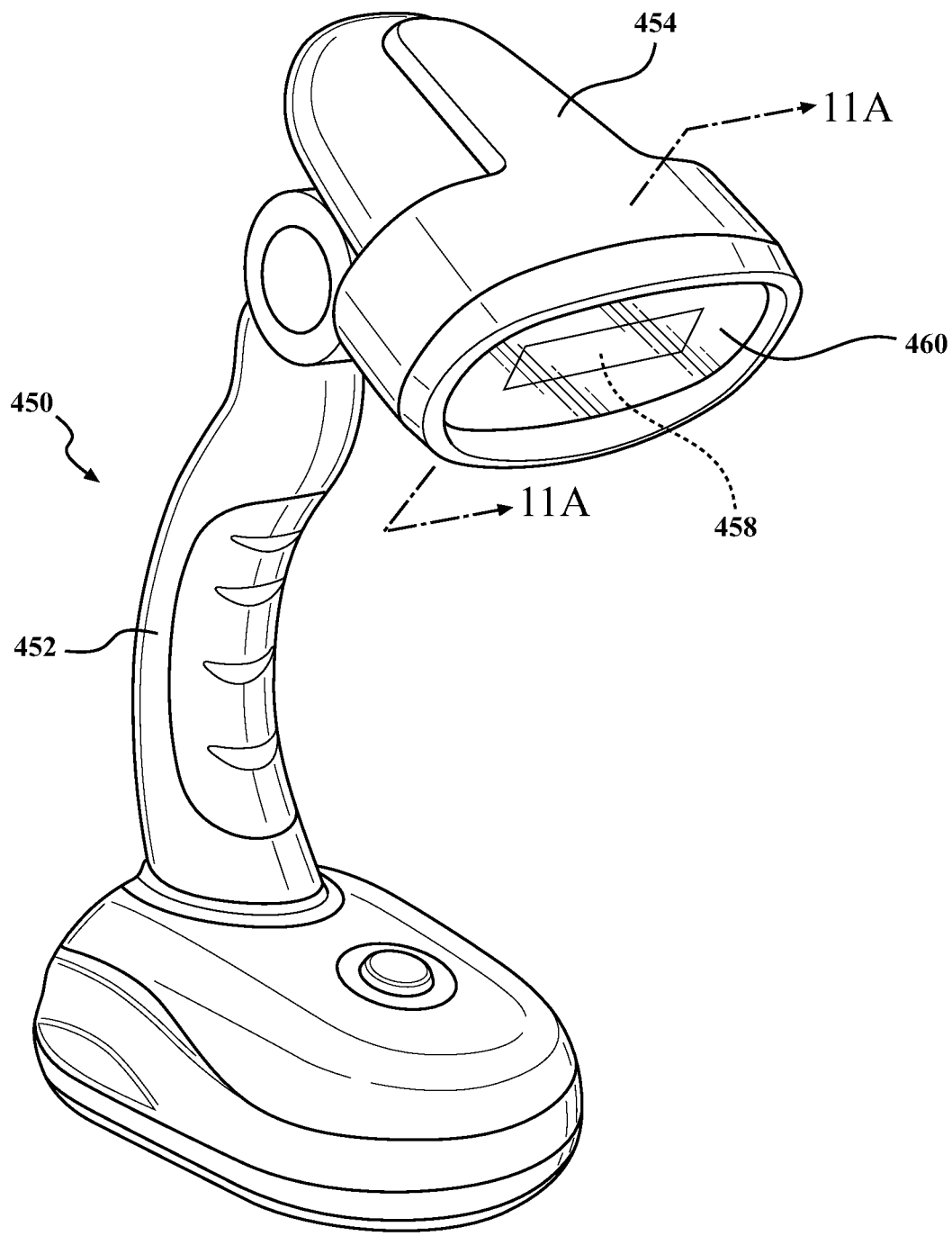
FIGS. 11 and 11A illustrate a product where the inventive layer can be integrated into a holder and have a secure placement distance from a body (or specifically targeted body part)
Figure 11A:
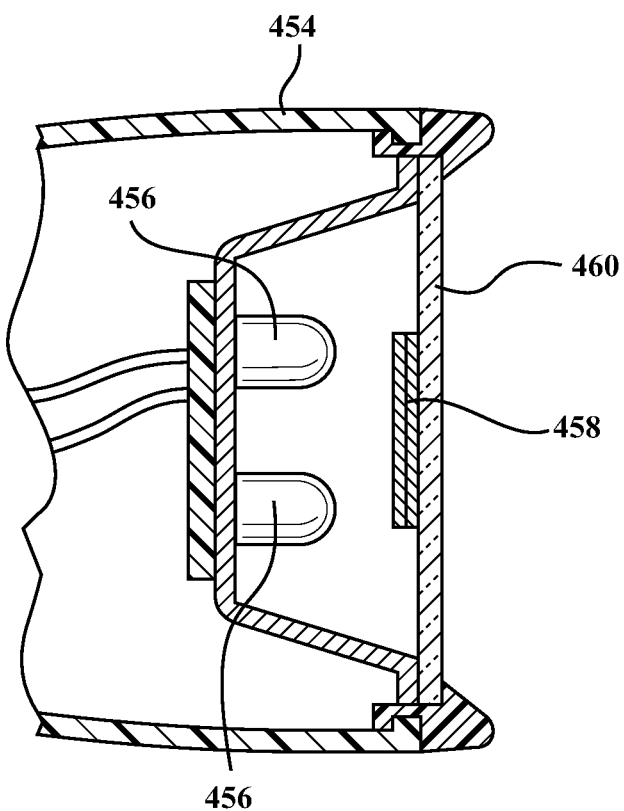

FIG. 11 illustrates the invention in a device 450 with a holder 452 where a part of the body, such as a hand or a wrist can be positioned in a relaxed manner adjacent the holder 452, and the device 450 can impart energy into the area of inflammatory pain or other light therapy as needed. As shown in FIG. 11A, the head portion 454 of the device 450 has LED bulbs 456 transmitting energy through a tri-layer 458 of PVDF coated copper with the polarizing layer against the lens 460 of the device.

Figure 12A:
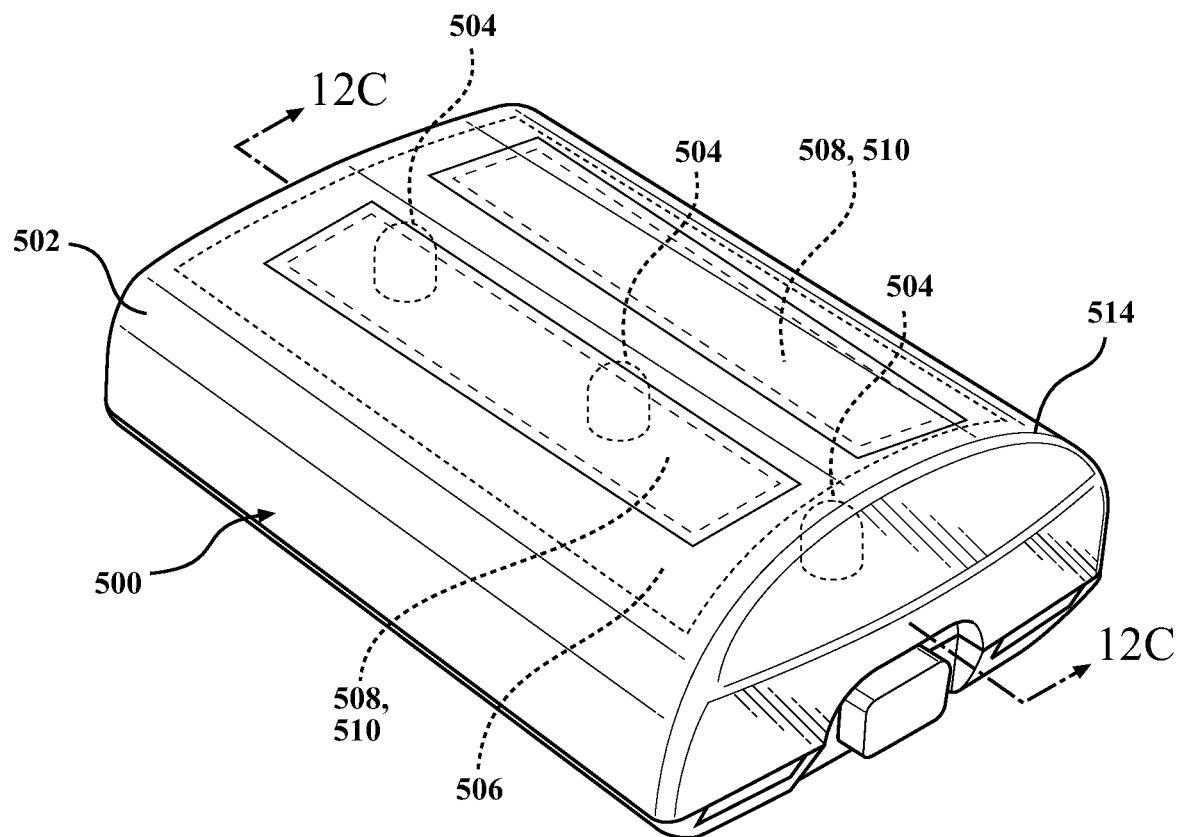
FIGS. 12A, 12B, and 12C illustrate an alternative light therapy product with the invention integrated into the product.
Figure 12B:
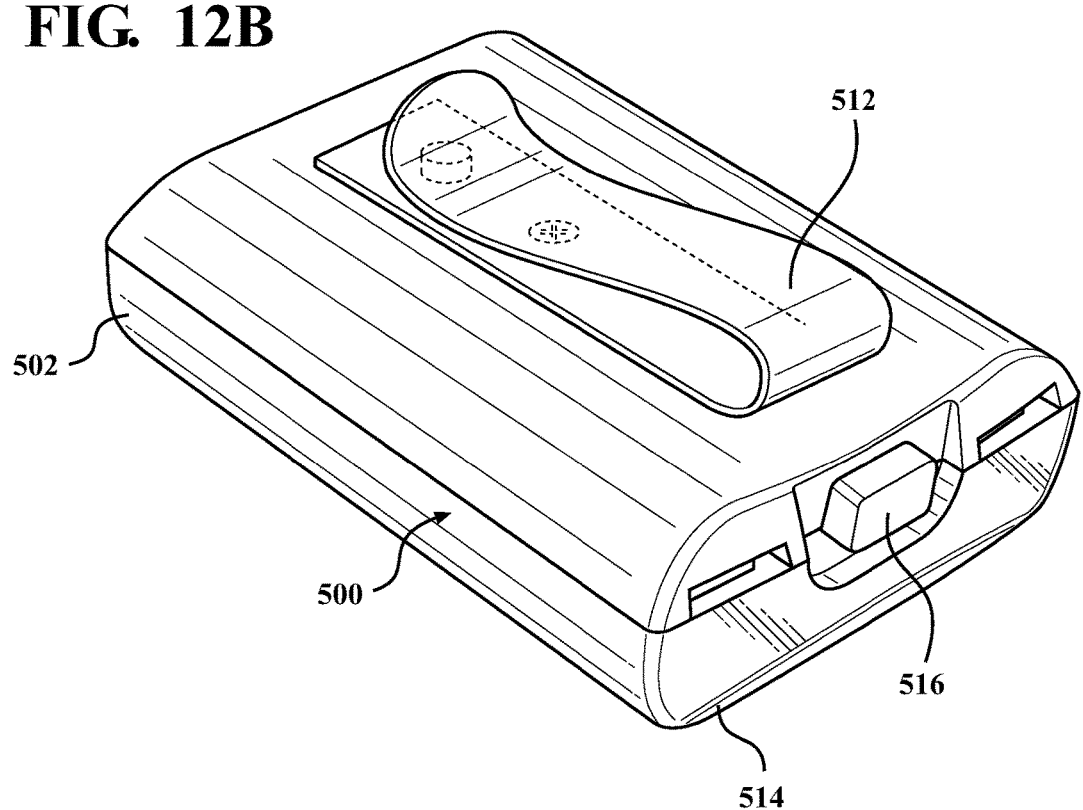
Figure 12C:
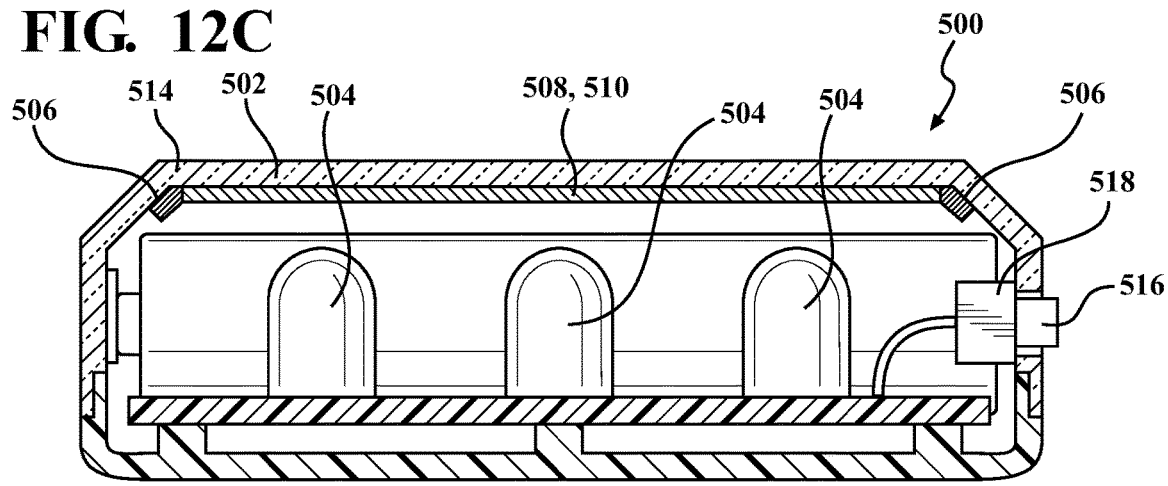

FIGS. 12A, 12B, and 12C illustrate another embodiment of the invention comprising a device 500 including a plastic case 502 preferably made of red plastic that permits the energy from LED bulbs 504 to pass after also passing through the tri-layer 506, 508, 510 in the manner shown. A clip 512 may be included with the device 500 to help position the device 500 or store the device 500 as needed. The polarizer layer 506 is disposed along the full length of the inside surface of the side 514 of the device 500 directed toward the body. Interior of the polarizer layer 506, two strips 508, 510 of a combined PVDF coated with copper are disposed. Preferably the strips (each 508, 510) are disposed on each side of the LED bulbs 504 so that a space exists between the strips (each 508, 510), although it is also anticipated that the strips (each 508, 510) could be one sheet extending across the LED bulbs 504 consistent with descriptions above in other embodiments. It is also anticipated that only one strip may be used and be effective as needed. The LED bulbs 504 can also be sprayed with a diffusion (Frosted Glass by RUST-OLEUM®). The LED bulbs 504 are controlled by a conventional button 516 connected to a control 518 for the LED bulbs 504 to provide the options of stay on continuously, flash/pulse, or shut off as the button 516 is pushed in a selected order. With this device, three ultrabrite red LED bulbs 504 can also be used if a heightened effect is desired for selected therapies. The device 500 is powered by two small batteries (not shown) as designed to power the LED bulbs 504 as needed or any other variation thereof.

Figure 13:
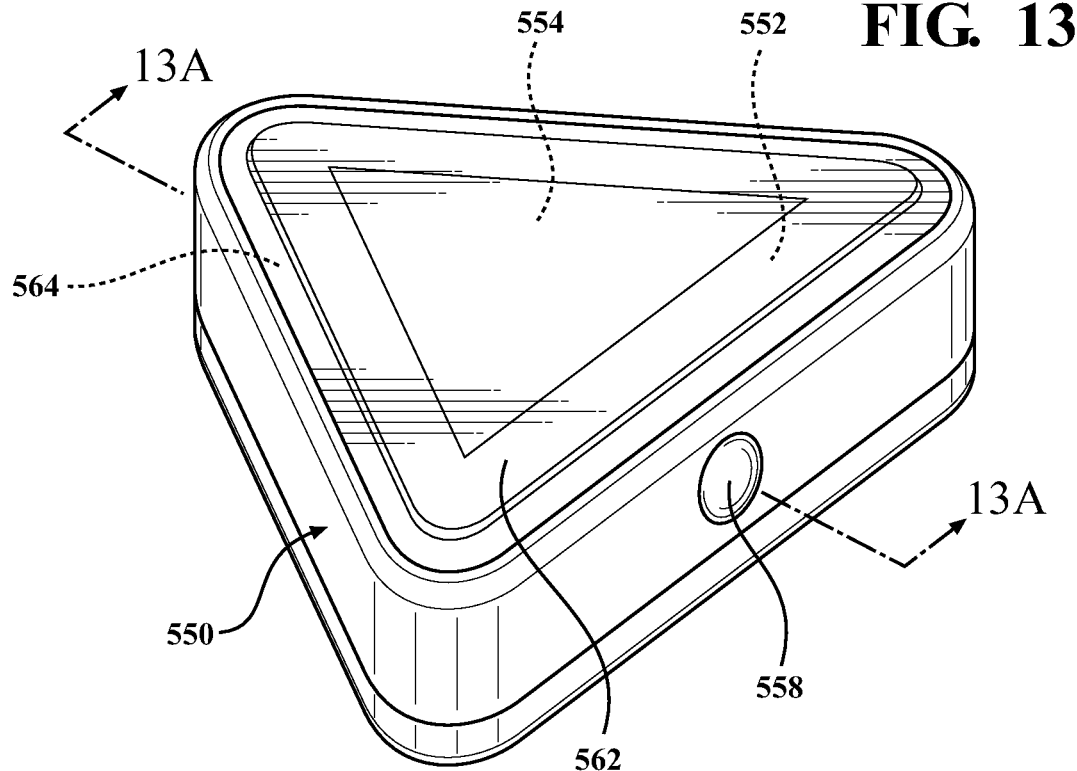
FIGS. 13 and 13A and 14 and 14A illustrate further variations of light therapy products integrating the invention into the product.
Figure 14:
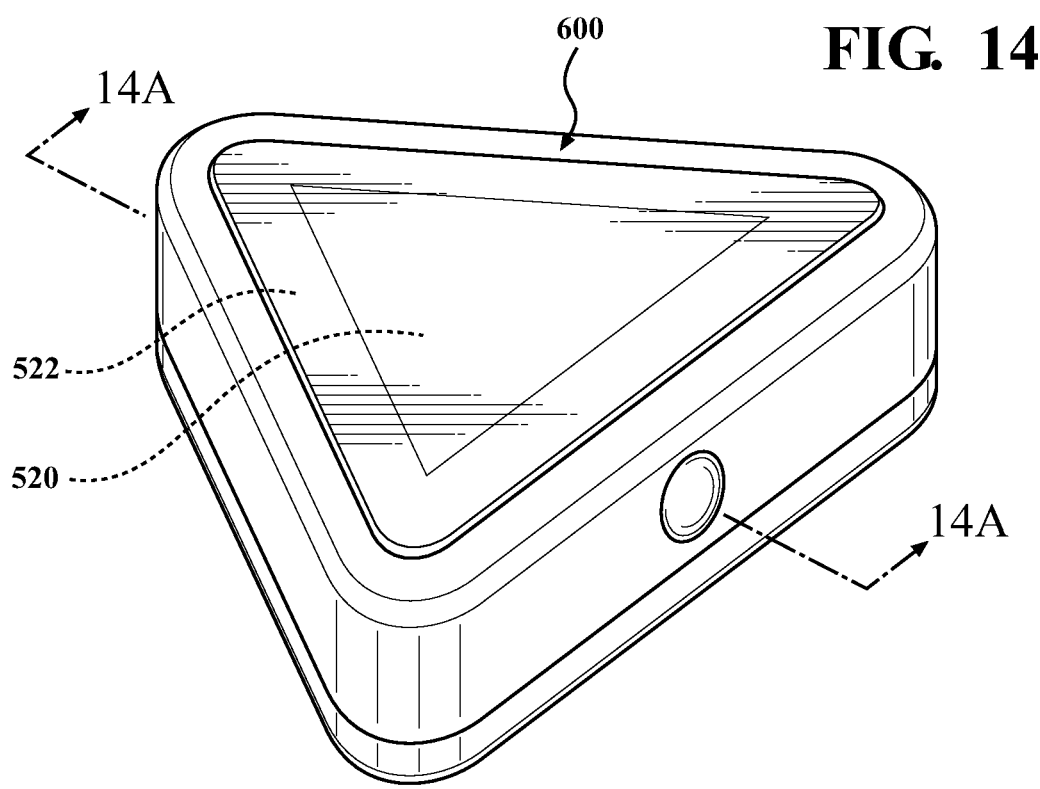
Figure 13A:
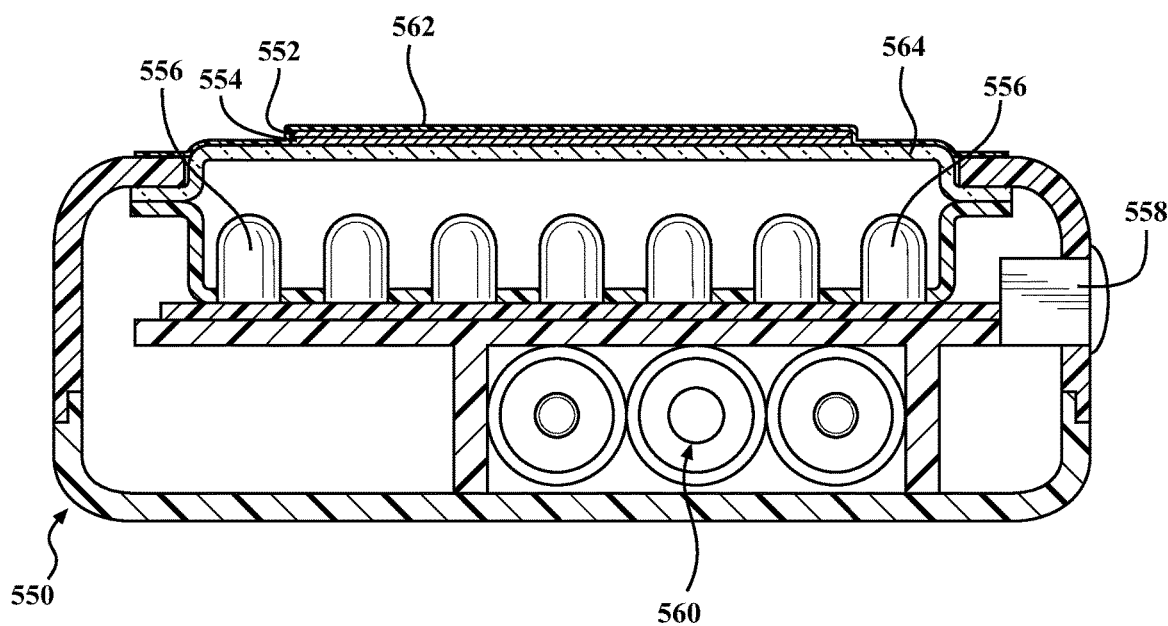

FIGS. 13 (and 13A) and FIGS. 14 (and 14A) illustrate additional alternatives where a typical LED bulb device 550 such as an emergency light triangle as sold by ACO Hardware or Harbor Freight, for example, can be transformed into a useful, therapeutic, light therapy device. In FIG. 13A, the layers are a polarizing layer 552 and a green cellulose layer 554 to provide nominal wavelength are disposed on the lens 564 of the device 550 and secured by tape 562 on the outside of the lens 564. When used with white LED bulbs 556, the unit has found effectiveness with PTSD and PSTD therapies. The device includes a control switch 558 and a power source/battery pack 560.

Figure 14A:
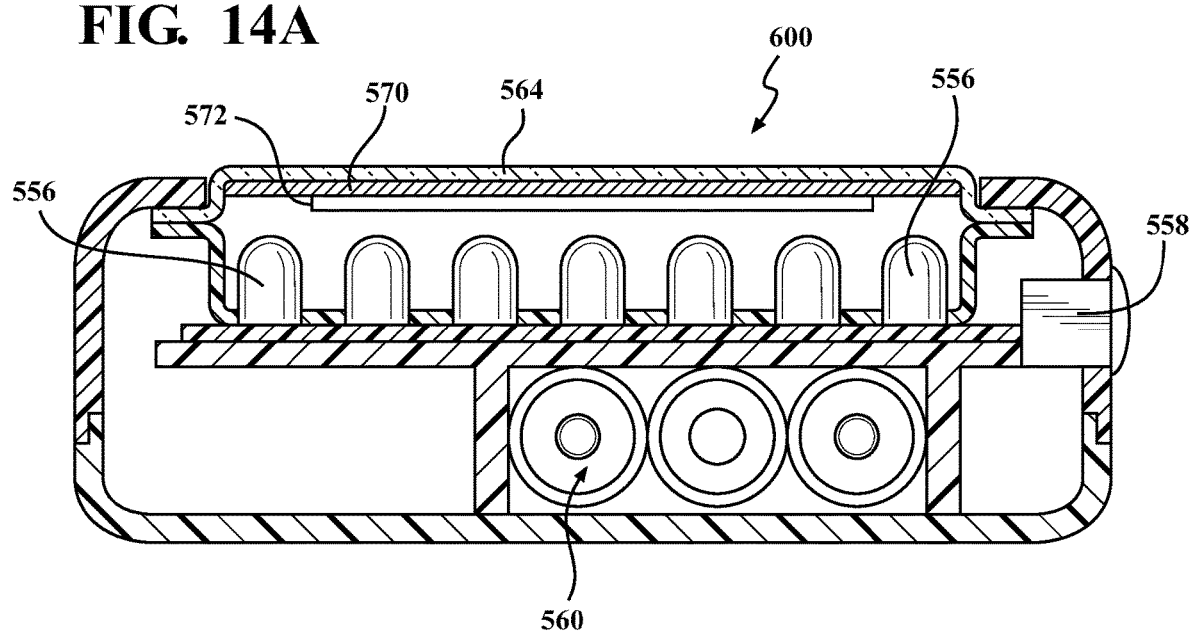

In FIG. 14A, a copper coated PVDF layer 572 is cut in the form of a triangle and set against the polarizer layer 570 also cut in the form of a larger triangle, both of which are disposed between the LED bulbs 556 and the lens 564 of the device 600. The polarizer layer 570 extends the full surface of the lens 564. The copper coated PVDF layer 572 does not. Each of the devices have a switch and control 558 which allows the device 600 to pulse, stay on, or turn off. The device 600 is powered by batteries 560.

Several embodiments have been discussed in the foregoing description. However, the embodiments discussed herein are not intended to be exhaustive or limit the invention to any particular form. For example, the above invention would not be limited to humans, but could be used effectively with various animals, particularly mammals. The terminology which has been used is intended to be in the nature of words of description rather than of limitation. Many modifications and variations are possible in light of the above teachings and the invention may be practiced otherwise than as specifically described.

With the previous research and studies in light therapy, and now with the added tri-polymer layer to accelerate pain relief, there should be no doubt as to the adaptation of such device to mankind's long-felt need for pain relief, particularly without ingesting anything in the body such as with various drug therapies.

What is claimed is:

1. A method of treating pain comprising the steps of:
placing a composite of noble metal, PVDF file and a polarizer in a package associated with a laser light source;
placing the package in association with a pain site on a body; and
waiting until the pain has diminished before removing the package from the site of the pain.

2. A method of treating pain comprising the steps of:
placing a composite of noble metal, PVDF file and a polarizer in a package including an LED source;
placing the package in association with a pain site on a body within one half inch of the skin of the body; and
waiting until the pain has diminished before removing the package from the site of the pain.

3. The method as set forth in claim 2, wherein said composite is disposed in a flexible package.

4. The method as set forth in claim 2, wherein the composite is integrated with the package and configured to be placed on the pain site on the body in a location defined by inflammatory pain emanating from the body.

5. The method as set forth in claim 2, wherein the composite comprises:
a first layer forming a base having a noble metal as an element of the material;
a second layer disposed on said first layer, wherein said second layer includes a PVDF film; and
a third layer disposed on said second layer including a polarizer; and
a laser light therapy source wherein the laser light is transmitted in association with said composite towards a human body.

6. The method as set forth in claim 5, wherein said composite is formed by spraying the first layer onto said second and third layers.

7. The method as set forth in claim 2, wherein said composite is disposed in a package to be held in place and directed to a source of inflammatory pain.

8. The method as set forth in claim 5, wherein layers are formed by taking said PVDF layer and dipping it on both sides into a bath of polyvinyl alcohol combined with iodine (to cause a polarizing effect) as a polarizing layer on both sides of the PVDF film layer, then spraying that combination with a conductive noble metal copper to create a layer on at least one side of the combination.

9. The method as set forth in claim 5, wherein all of the layers of the composite have a polymeric foundation.

10. The method as set forth in claim 1, wherein said composite is disposed in a package that can be configured to come into contact with the outer skin of said body.

11. The method as set forth in claim 1, wherein the composite is integrated with the package and configured to be placed on the pain site on the body in a location defined by inflammatory pain emanating from an animal.

12. The method as set forth in claim 1, wherein said package is configured for placement at an acupuncture meridian for treatment.

13. The method as set forth in claim 1, further comprising a laser light therapy source wherein the laser light source is LED.

14. The method as set forth in claim 1, wherein the composite comprises:
a first layer forming a base having a noble metal as an element of the material;
a second layer disposed on said first layer, wherein said second layer includes a PVDF film; and
a third layer disposed on said second layer including a polarizer; and
a laser light therapy source wherein the laser light is transmitted in association with said composite towards a human body.

15. The method as set forth in claim 14, wherein all of the layers of the composite have a polymeric foundation.

16. The method as set forth in claim 14, wherein layers are formed by taking said PVDF layer and dipping it on both sides into a bath of polyvinyl alcohol combined with iodine (to cause a polarizing effect) as a polarizing layer on both sides of the PVDF film layer, then spraying that combination with a conductive noble metal copper to create a layer on at least one side of the combination.

\* \* \* \* \*